United States Patent [19]

Schmidt et al.

[11] 4,021,542

[45] May 3, 1977

[54] DERIVATIVES OF HYDRAZINO-MONOSACCHARIDES AND ALDOHEXOSES WHICH ARE USEFUL AS INTERMEDIATES FOR PREPARING COMPOUNDS OR AS COMPOUNDS WHICH LOWER THE URIC ACID

[75] Inventors: Richard Schmidt, Stuttgart; Kurt Klemm, Allensbach, both of Germany

[73] Assignee: Byk Gulden Lomberg Chemische Fabrik GmbH, Germany

[22] Filed: Nov. 26, 1974

[21] Appl. No.: 527,435

Related U.S. Application Data

[63] Continuation-in-part of Ser. No. 474,452, May 29, 1974, abandoned.

[30] Foreign Application Priority Data

June 1, 1973  Luxembourg .......................... 67726

[52] U.S. Cl. ................................ 424/180; 536/22; 536/23

[51] Int. Cl.$^2$ ................. A61K 31/70; C07H 19/04
[58] Field of Search ............... 260/211 R, 211.5 R, 260/310 R; 424/180; 536/22, 23, 24

[56] References Cited

UNITED STATES PATENTS

| | | | |
|---|---|---|---|
| 3,567,735 | 3/1971 | Druey et al. | 260/310 R |
| 3,658,838 | 4/1972 | Kiehne et al. | 260/310 R |
| 3,682,913 | 8/1972 | Sturm | 260/256.4 N |
| 3,704,241 | 11/1972 | Noguchi et al. | 260/310 R |

*Primary Examiner*—Johnnie R. Brown
*Attorney, Agent, or Firm*—Berman, Aisenberg & Platt

[57] ABSTRACT

Substituted hydrazino- and pyrazolo-aldopentoses and aldohexoses, which are useful as intermediates for preparing compounds, as compounds which lower the uric acid level in the blood, and as bactericides, are provided. The substituted hydrazino compounds also enter into chemical reactions which are not possible with their unsubstituted counterparts.

39 Claims, No Drawings

DERIVATIVES OF HYDRAZINO-MONOSACCHARIDES AND ALDOHEXOSES WHICH ARE USEFUL AS INTERMEDIATES FOR PREPARING COMPOUNDS OR AS COMPOUNDS WHICH LOWER THE URIC ACID

RELATED APPLICATION

This application is a continuation-in-part of Application Ser. No. 474,452, filed May 29, 1974 now abandoned.

BACKGROUND

Published studies of Stroch et al. (Chem. Ber. 98 [1965] 1404), Haas et al. (J. Am. Chem. Soc. 84 [1962] 4910) and Tipson (J. Org. Chem. 27 [1962] 2272) refer to reaction products of unsubstituted D-ribose with hydrazine, for example unsubstituted D-hydrazino-ribose.

SUMMARY OF THE INVENTION

The invention is directed to hydrazino- and pyrazoloaldopentoses and aldohexoses, synthesis thereof, pharmaceutical preparations having at least one pyrazolo-aldopentose or pyrazolo-aldohexose as an active ingredient therein and the use of such pharmaceutical preparations, particularly in the treatment of gout.

DETAILS

The subject matter of the present application comprises compounds of formula I

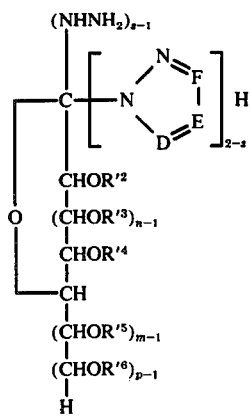

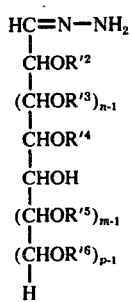

wherein
s is a positive whole number of at most 2;
D is =C(X)—, =C(NH$_2$)— or =N—;
E is =C(Y)— or =N—;
F is =C(X)— or =N—;
W is —H, —OH or —NH$_2$;
X is one of the meanings of Z or, together with Y, -N=CH-N=C(W)-;
Y is -H, carbethoxy, cyano, carbamoyl, formylcarbamoyl, benzoylcarbamoyl or, together with with one X, -C(W)=N-CH=N-;
Z is -H, alkyl or phenyl;
each of
n, m and p is a positive whole number of at most 2, the sum of n+ m+ p is at least 4, and at least one of n, m and p is 1;
each of
R'$^2$, R'$^3$, R'$^4$, R'$^5$, and R'$^6$ is, independently, —H or a member selected from the group consisting of alkyl, an ethylenically-unsaturated hydrocarbon radical, aryl, aralkyl, and cycloalkyl having from 3 to 6 ring carbon atoms, with the proviso that at least one of R'$^2$, R'$^3$, R'$^4$, R'$^5$, and R'$^6$ which is present in the compound has a meaning other than -H, and in the case of which also, if sterically possible, two respective radicals R'$^2$, R'$^3$, R'$^4$, R'$^5$ or R'$^6$ together can denote an alkylidene, preferably isopropylidene (≡propane-2-ylidene) radical or a benzylidene radical. [The open-ring form, as defined in the sense of this invention, is depicted by formula IB. The compounds of formula I, wherein s denotes 2, and of formula IB coexist as tautomers in equilibrium (so-called Oxocyclo-Tautomerie, see H. Beyer, "Lehrbuch der Organischen Chemie", 15./16. Auflage, S. Hirzel Verlag Leipzig, 1968, pages 319 ff.).]

In particular in formula I the radicals R'$^2$, R'$^3$, R'$^4$, R'$^5$, and/or R'$^6$, in so far as they are different from hydrogen, denote radicals which can readily be split off, for example hydrogenolytically or hydrolytically.

Alkyl and ethylenically-unsaturated hydrocarbon radicals have up to 7 carbon atoms and are straight chained or branch chained. An alkyl radical is for example, a methyl, ethyl, a propyl, isopropyl, butyl, isobutyl, sec.-butyl or tert.-butyl, pentyl, isopentyl, 1— or 2-methylbutyl, tert.-pentyl, hexyl, isohexyl, 1—, 2— or 3-methylpentyl, 1-, 2- or 3-ethylbutyl, 1,2-, 1,3- or 2,3-dimethylbutyl, heptyl or isoheptyl group; an ethylenically-unsaturated hydrocarbon radical, for example a vinyl, allyl, 2-methyl-allyl, propen-1-yl, butene-1- or 2-yl, penten -1-, 2- or 3-yl, hexenyl or 2-methyl-propen-1-yl group.

Alkylidene radicals with up to 7 carbon atoms are those e.g. which are derived from the above mentioned alkyl radicals with up to 7 carbon atoms by replacement of the -yl ending by an-ylidene ending.

An aryl radical is, for example a phenyl or naphthyl (α- or β-) radical, the first being preferred, non-substituted or substituted by alkyl having up to seven carbon atoms, halogen, (preferably chlorine), nitro, trifluoromethyl, alkoxy having up to seven carbon atoms, hydroxy, sulfo, sulfino, alkylsulfone having up to seven carbon atoms, alkoxycarbonyl having up to seven carbon atoms, alkylamino having up to seven carbon atoms, dialkylamino having up to seven carbon atoms or carbamoyl.

In an aralkyl group the alkyl group can have one of the meanings given for a straight-chained or branch chained alkyl group and the aryl radical can have one of the meanings given for aryl; preferably an aralkyl group is a group which can easily be split off, as for example a benzhydryl or trityl and more particularly benzyl group, and also an α- or β-naphthylmethyl group possibly substituted like aryl. As a substituent chlorine is preferred.

A cycloalkyl group with 3 to 6 carbon atoms is, for example a cyclopropyl, 2- or 3-methyl-cyclopentyl or preferably a cyclohexyl group.

A benzylidene radical can be substituted in the phenyl radical by the radicals specified in the case of aryl, but the radical is preferably unsubstituted.

Hydrozinoaldopentoses of the general formula I ($s = 2$) are for example hydrazino-lyxoses or hydrazinoxyloses, preferably hydrazinoarabinoses and more particularly hydrozinoriboses, hydrozinoaldohexoses the general formula I ($s = 2$) as for example, hydrazinoalloses, hydrazinoaltroses, hydrazinomannoses, hydrazinoguloses, hydrazinoidoses, hydrazinotaloses or hydrazinogalactoses, and preferably hydrazinoglucoses.

The subject matter of the invention also comprises a method for the production of compounds of the general formula I ($s = 2$) or of their open ring forms (IB), which is characterized in that the compound of the general formula II or its open ring form (IIB) or a mixture of these both tautomers is reacted with hydrazine,

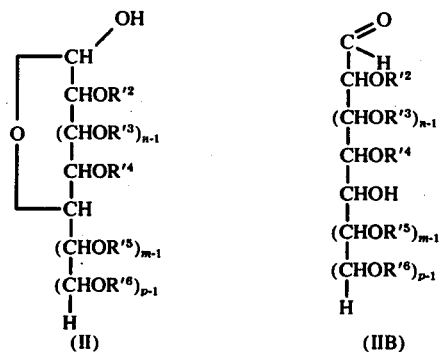

in which $n$, $m$, $p$, $R'^2$, $R'^3$, $R'^4$, $R'^5$, and $R'^6$ have the meanings indicated for formula I and at least one of the radicals must be different from a hydrogen atom.

The reaction of II or IIB or a mixture thereof with hydrazine is preferably carried out in an inert organic or organic-aqueous medium; the reaction can be carried out at room temperature or while heating up to approximately 150° C, preferably however while cooling down to approximately -20° C and at normal pressure or at a raised pressure and preferably under a protective gas, for example nitrogen, atmosphere.

Instead of anhydrous hydrazine it is also possible to use hydrazine hydrate with just as satisfactory results; in the case of the preparation of hydrazinohexases hydrazino-hexoses, more particularly hydrozinoglucoses, it is however convenient to operate under anhydrous conditions with hydrazine in an inert organic solvent.

In this respect it can be convenient to operate in the presence of an acidic catalyst, for example small quantities of an organic or inorganic acid, as for example a hydrochloric acid.

Inert organic solvents suitable for this purpose are, in particular, alcohols, such as ethanol, isopropanol, polar fatty acid amides, for example dimethylformamide, dimethylsulfoxide and more particularly methanol or tetrahydrofuran.

The starting materials of the formulae, II and IIB are known or are produced in accordance with conventional methods from available starting material. The compounds of the formulae II and IIB are produced for example, from 1-methyl-glycosides by etherifying, possibly in a selective manner, of the free hydroxyl groups in accordance with methods conventional in sugar chemistry and thereafter splitting off of the glycosidic methyl group (see Barker and Fletcher, J. Org. Chem. 26 [1961] 4605).

The compounds in accordance with the invention of the formula I, in which s is 2, are valuable chemical intermediates for the production of other compounds, and more particularly of pharmacologicaly-active compounds. It has thus been found that with compounds of the general formula I, in which s is 2, chemical reactions are carried out which are not capable of being carried out with unsubstituted hydrazino-sugars.

It was surprising that hydrazino-sugars of the formula I ($s = 2$) react with carbonyl compounds, for example with p-nitro-benzaldehyde, like hydrazine to form the corresponding hydrazone, while this reaction is not possible with non-substituted hydrazino-pentoses or hydrazino-hexoses of formula I, in which s is 2 and $R'^2$, $R'^3$, $R'^4$, $R'^5$ and $R'^6$ all denote hydrogen.

In contrast to non-substituted hydrazinopentoses and hydrazino-hexoses it is therefore possible to carry out with the compounds of the formula I, in which s is 2, also such pyrazole syntheses as are known for hydrazine in the literature [see, for example German Patent Specification No. (Auslegeschrift) 1,070,635, German Patent Specification No. (Offenlegungsschrift) 1,904,894, German Patent Specification No. (Offenlegungsschrift) 1,720,024, German Patent Specification No. (Offenlegungsschrift) 1,814,082]. For example in this manner ribosides of biologically-active pyrazolopyrimidines, for example of allopurinol [see German Patent No. Specification (Offenlegungsschrift) 1,927,136]are prepared in an advantageous manner.

The subject matter of the present invention also therefore comprises a method for producing a compound of the general formula I, wherein s is 1, or a counterpart thereof, the counterpart in each instant being the corresponding compound wherein each of $R'^2$, $R'^3$, $R'^4$, $R'^5$ and $R'^6$ is hydrogen, and in which the residue

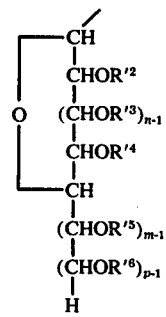

is preferably one of the hydrazino-glucose derivatives mentioned below as being preferred of the formula Ia or of the hydrazino-arabinose derivatives of the formula Ib, and primarily a radical derived from the hydrazino-ribose derivatives of the formula Ic, and in which the residue (A)

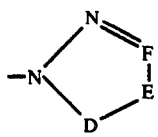

is preferably one in which a. D is =C(NH$_2$)—, E is =C(Y)—, Y is carbethoxy, cyano, carbamoyl, formyl carbamoyl or benzoylcarbamoyl, and F is =CH—; or
b. D and F are different or, preferably, the same and denote =C(X)—, X is H, alkyl with preferably up to 3 carbon atoms, or phenyl, and E is = CH—; or
c. F is =C(Z)—, Z is alkyl or phenyl and preferably H, E is =C(Y) and D is =C(X)—, X and Y together denote -N=CH-N=C(W)—, and W is OH or NH$_2$; or also
d. D is =C(NH)$_2$—, E is =N—, F is =C(Z)—, and Z is H, phenyl or particularly alkyl with preferably up to 3 carbon atoms.

The method is characterized in that a compound of formula I, in which s is 2, is reacted with a component forming the ring system A together with I and, if desired, in a conventional manner, [see, for example, German Patent Specifications (Offenlegungsschrift No.) 1,720,024, and 1,814,082] a further ring system is condensed on, and if R'$^2$, R'$^3$, R'$^4$, R'$^5$ and/or R'$^6$ in the formula I (s = 1) denote a hydrogen atom, compounds of the formula I (s = 2), are used as a basis in which the radicals, if they are different from hydrogen, denote a radical which can be subsequently split off or split off during reaction, such as benzhydryl, or preferably trityl or more particularly benzyl or two radicals together denote benzylidene, and preferably isoproylidene, and, if required, these radicals are subsequently split off. The condensation of a further ring system comprises condensing an alicyclic hydrocarbon ring or a heterocyclic ring onto the 3,4- or preferably onto the 4,5-position of the aromatic ring A

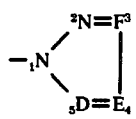

in which F and E is =C(H)—, D is =N— or =C(X)—, and X is H, alkyl or phenyl (in the case of 3,4-condensation), or in which each of E and D is =C(H)—, F is =N— or =C(Z)—, and Z is H, alkyl or phenyl (in the case of 4,5-condensation), and in which the condensed ring system built up during the condensation preferably is the ring system A stated on page 11 under (c). In accordance with the specific reactions conditions and the substituents present in this respect a co-condensation of a further ring system with the aromatic ring A can occur even in the same reaction step as the formation of A without the non-condensed compound having to be isolated from the reaction mixture.

The reaction of I (s = 2) with a component building up the pyrazole system is preferably carried out in an inert organic solvent. In accordance with the constitution of the desired final product I (s = 1) the operation is carried out while cooling down to approximately −20° C, at normal pressure or at a raised pressure and possibly under a protective gas, for example nitrogen, atmosphere. In this respect it is convenient to carry out the reaction in the presence of condensing agents for example in the presence of catalytic quantities of an organic or inorganic acid such as hydrochloric acid, of N,N'-dicyclohexylcarbodiimide.

Inert organic solvents suitable for this reaction are for example, aromatic hydrocarbons, such as toluene, halogenated hydrocarbons, e.g. chloroform, and alcohols, more particularly methanol or ethanol or cyclic ethers, such as tetrahydrofuran.

As components forming the ring system A together with I (s = 2), compounds come into question which have the partial structure

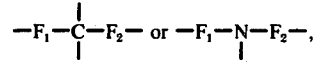

wherein F$_1$ and F$_2$ denote functional groups, with which hydrazine reacts by condensation or addition to form the ring system, and in which F$_1$ and F$_2$ preferably denote a

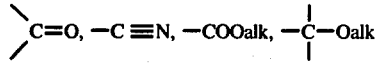

or —COOH group or derivatives thereof, e.g. amides and imides, and wherein alk is alkyl group with up to seven, preferably up to three, carbon atoms. Such compounds are preferably compounds which are used for synthesis of pyrazole systems by reaction with hydrazine, as described in German Patent Specification (Auslegeschrift) No. 1,070,635, German Patent Specification (Offenlegungsschrift) No. 1,904,894, German Patent Specification (Offenlegungsschrift) No. 1,720,024, German Patent Specification (Offenlegungsschrift) No. 1,814,082, as for example β-dicarbonyl compounds, for example acetylacetone or heptadienone-3,5 or dibenzoylmethane, β-oxo-carbonitriles, for example acetyl-acetonitrile, α-cyano-α-formylacetic acid or their functional acid and/or aldehyde derivatives, for example ethoxymethylenemalodinitrile, ethoxymethylenecyanoacetic acid ethyl ester, β-ethoxy-α-cyano-N-(formyl or benzoyl)acryloamide, β-morpholino-β-cyanoacrylamide or 2-ethoxyacrolein, and furthermore also alkyl esters of N-cyanoalkanimidic acids in which alkane and alkyl have up to seven, preferably up to three, carbon atoms, as for example ethyl N-cyano-ethanimidoate or ethyl N-cyano-propanimidoate.

A substantial advantage of the method in accordance with the invention resides in that by a suitable choice of the substituents R'$^2$, R'$^3$, R'$^4$, R'$^5$ and R'$^6$ the pure α-anomers and in some cases also the α-anomers, of the compounds I, in which s is 1, are obtained with good yields. Thus, for example in the case of the reaction of 1-hydrazino-2,3,5-tri-O-benzyl-D-ribose or 1-hydrazino-2,3-O-isopropylidene-D-ribose the biologically more valuable β-ribosides are obtained, while in the case of the reaction of 1-hydrazino-2,3,4,6-tetra-O-benzyl-D-glucose the β-glucosides are obtained and in the case of the reaction of 1-hydrazino-2,3,5-tri-O-benzyl-D-arabinose the α-arabinosides are obtained. As a result the tedious separation of an anomer mixture in accordance with conventional methods is no longer necessary.

Furthermore, in accordance with this method glycosides are exclusively obtained in the case of which the sugar radical is always tied to the N-1-nitrogen atom, while with methods involving subsequent glycosylation of a pyrazole system, mixture may be produced.

The splitting off of one of the $R'^2$, $R'^3$, $R'^4$, $R'^5$ and/or $R'^6$ radical is, e.g., carried out in accordance with conventional methods, as for example by hydrogenolysis or hydrolysis. Preferably as groups which can be split off use is made of aralkyl groups which can be readily be split off, as for example benzhydryl, benzylidene, preferably trityl and more especially benzyl groups, or alkylidene, preferably isopropylidene, groups. The latter are split off from the reaction products I in a conventional manner, a benzyl radical for example by treatment with nascent or catalytically activated hydrogen, such as hydrogen in the presence of a noble metal, as for example palladium catalyst, possibly in the presence of acids, as for example hydrogen chloride, an iropropylidene radical or also a trityl radical, for example by hydrolysis in the presence of an acid. In accordance with the respective reaction conditions in this case all the radicals or only some of them can be split off. The reaction conditions are selected therefore in view of all other substituents of the molecule.

If in accordance with the method of the invention for example 3-ethoxy-2-cyano-N-formyl-acryloamide [German Patent Specification (Offenlengungsschrift) 1,814,082] is reacted with a compound of the formula I ($s = 2$), for example with 1-hydrazino-2,3,5-tri-O-benzyl-D-ribose or 1-hydrazino-2,3-O-isopropylidene-D-ribose, it is possible to obtain, preferably after splitting off of the benzyl or isopropylidene radical, new pyrazole-ribosides of the formula I ($s = 1$), with valuable pharmacological properties.

In this manner are obtained for example 5-amino-4-(N-formylcarbamoyl)-1-(2,3,5-tri-O-benzyl-$\beta$-D-ribofuranosyl)pyrazole, 5-amino-4-(N-formylcarbamoyl)-1-(2,3-O-isopropylidene-$\beta$-D-ribofuranosyl)-pyrazole or 5-amino-4-carbamoyl-1-(2,3-O-isopropylidene-$\beta$-D-ribofuranosyl)pyrazole.

The compounds of formula I, in which s is 1, especially the preferably-produced compounds of formula I specified on page 10/11 and more particularly 4-hydroxy-1-($\beta$-D-ribofuranosyl)pyrazolo-[3,4-d]pyrimidine and the compounds listed in page 16, lines 18 to 23, primarily in the form with an unsubstituted ribose radical ($R'^2$, $R'^4$, $R'^5$ and $R'^6$ each are hydrogen) and also their counterparts, in which the ribose residue is replaced by the glucose or arabinose residue, have more particularly an inhibiting action which is novel for such substances, with respect to the ferment xanthineoxidase and have an extremely low toxicity. The new compounds effect uric-acid level reduction in blood of a warm-blooded animal, for example they bring about [in doses of 10 to 100 mg/kg in the case of rats] on oral administration a pronounced lowering of the uric-acid level in the blood. The novel compounds and their pharmacologically-compatible salts with inorganic and organic acids are useful as valuable therapeutic substances, preferably for the treatment of gout and also as agents for treatment of coronary insufficiency with an anti-arrhythmic action. Furthermore, compounds of formula I, in which $s$ is 1 or also 2, are valuable bactericides and/or fungicides (cf. U.S. Pat. Specification No. 3,598,807). For example they stop the growing of gram-positive bacteria (e.g. Strepto Gr. A) or the growing of yeast (e.g. C. albicans) in a minimal concentration of 500 –1000γml of nutrient broth.

Medicaments or pharmaceutical compositions which contain one or more compounds of formula I ($s = 1$) in a free form or in the form of a pharmacologically-compatible acidaddition salt) as active substance can, but need not, contain other chemically- and physiologically-compatible pharmacologically-active substances. Such medicaments are produced in a conventional manner by combining the active substance with a pharmaceutical vehicle, such as a filter, a diluent, a correcting agent and/or components conventional for medicaments. The medicaments are produced in a solid-dosage form as, e.g., tablets or capsules, or in a liquid form as, e.g., solution or suspensions. The pharmaceutical vehicle can also contain conventional diluent and tablet-forming additions, such as cellulose powder, maize starch, lactose and talcum, as conventional for such purposes.

The production of a pharmaceutical preparation is carried out in the conventional manner, for example, by means of conventional mixing, granulating and coating methods. The pharmaceutical preparations contain from approximately 0.1% to 75%, preferably from 1% to approximately 50%, by weight of the active substance. Administration is external, for example oral, or parenteral; individual doses of active substances are from 10 to 100mg/kg of body weight. For application in human medicine these doses correspond to an individual dose of approximately 50 to 1000 mg/kg of active substance per day.

The indicated doses are administered 1 to 4 times daily, for example at mealtimes and/or in the evening. The individual dose, the frequency of administration and the duration of treatment are determined by the nature and severity of the illness. A daily oral dose of, e.g., 300 mg/kg of a compound of formula I($s=1$) is generally adequate for the treatment of an attack of gout.

The invention thus relates to medicaments, particularly for treating gout but also for cardiac insufficiency and arrhythmia. The medicaments are characterized by a content of one or more compounds of formula I($s=1$) in free form or in the form of a pharmacologically-compatible salt. The invention further relates to a method of reducing uric-acid level in blood of a mammal which comprises administering to the mammal a non-toxic, but uric-acid-level reducing, amount of such a medicament.

Bactericidal and fungicidal compositions contain one or more of the compounds of the general formula I, in which $s$ is 1 or also 2, in a concentration of 10 to 10,000 parts per million, preferably 100 to 1000 parts per million and usual carriers therefore. The compositions are solid, such as a powder, or liquid, such as a suspension, emulsion or solution. Useful carriers for powders are for example China clay, starch, talcum, calcium phosphate and solid high-molecular polymers. Carriers for suspensions, emulsions and solutions are solvents e.g. water, organic solvents, such as paraffins, plant oils and glycols, and non-ionic or anionic emulsifiers, such as polyoxyethylene fatty acids and alkyl- or arylsulfonates, and dispersing agents, such as lignin. The carriers are used in conventional proportions. If the compositions are to be diluted prior to actual use, the concentration of the active igredient is initially correspondingly higher.

Compounds of general formula I, in which s is 2, are valuable starting compounds as regards the synthesis of the compounds of formula I, in which s is 1, for example particularly valuable products are hydrazino-D-glucoses of the formula Ia

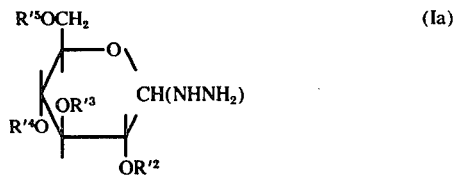

hydrazino-D-arabinoses of the formula Ib

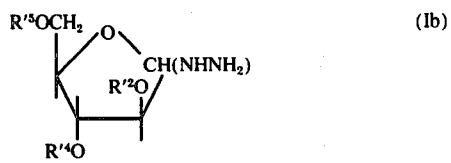

and, more particularly hydrazino-D-riboses of general formula Ic

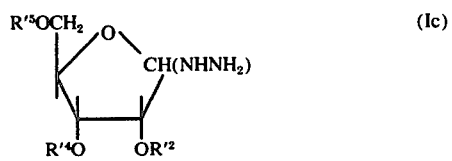

or their open ring forms, [cf. formula Ib] in which R'², R'³, R'⁴ and R'⁵ have the meanings given in formula I, and preferably (having regard to the synthesis of biologically especially effective compounds of formula I, in which s is 1 and in which each of the radicals R'², R'³, R'⁴, R'⁵ and R'⁶ is a hydrogen atom), in so far as they do not denote a hydrogen atom, denote a group which can be readily split off, for example hydrogenolytically or hydrolytically, and more particularly an aralkyl group which can readily be split off, as for example a possibly substituted benzhydryl or preferably trityl and more particularly benzyl group, or two respective radicals, if sterically possible, can denote a benzylidene and more particularly an isopropylidene group, in the case of which in the formula Ia more particularly at least R'² and/or R'⁵ are other than a hydrogen atom, in formula Ib preferably at least R'⁵ and/or R'² are other than a hydrogen atom, and in formula Ic preferably at least R'⁵ and/or R'² are other than a hydrogen atom or R'⁴ and R'² together form an alkylidene, more particularly isopropylidene group, and preferably 1-hydrazino-2,3,4,6-tetra-O-benzyl-D-glucose, 1-hydrazino-2,3,4-tri-O-benzyl-D-arabinose and more particularly 1-hydrazino-5-O-trityl-D-ribose or 1-hydrazino-2,3-O-isopropylidene -5-O-trityl-D-ribose and primarily 1-hydrazino-2,3-O-isopropylidene-D-ribose or 1-hydrazino-2,3,5-tri-O-benzyl-D-ribose.

The invention also relates to those forms of embodiments of the method in the case of which one starts from a compound which can be obtained at any stage of the method as an intermediate product and then carries out the additional method steps or the method is interrupted at any particular stage, or a compound used as a starting material is formed under the reaction conditions or is used in the form of a reactive derivative or salt.

As starting materials for all methods of the present invention it is preferred to use those which lead to the compounds described above as being especially valuable. The reaction conditions of the methods are in this respect selected according to the constitution, configuration and substitution of the reaction partners.

The following examples explain the invention in more detail without restricting it. Silicagel (Macherey & Nagel/Duren, West Germany, grain size 0.05–2mm/70-325 mesh ASTM) is used for chromatographic separations.

EXAMPLE 1

1-methyl-β-D-ribofuranoside 1-methyl-β-D-ribofuranoside was produced in accordance with the method of Barker and Fletcher[1]. The authors also described in their method a path leading to crystallisation of 1-methyl-β-D-ribofuranoside. This step was not carried out; instead the sirup produced after purfication by ion exchanger and ethyl acetate/active charcoal was used directly for further reaction.

EXAMPLE 2

1-methyl-2,3,5-tri-O-benzyl-β-D-ribofuranoside[1]

150g (5 moles) of 80% sodium hydride suspension in oil are dried three times each time with a 200 ml portion of absolute tetrahydrofuran, and then placed in a 2 l three-necked flask. 50 g (0305 mole) of 1-methyl-β-D-ribofuranoside dissolved in 500 ml of absolute tetrahydrofuran are added, and the reaction product immediately clumps together (break up with spatula). While stirring, 460 g (363 moles) of distilled benzyl chloride are added and then stirring is carried out for 24 hours at 80° C. Then residual sodium hydride and formed NaCl are filtered off (lasting about 2 days). The filter residue is then subjected to centrifuging. The yellow solution obtained is freed in a rotary evaporator from residual tetrahydrofuran and benzyl chloride. The yellow oil remaining is distilled in a metal bath under oil pump vacuum. Boiling point (10⁻²Torr) approximately 235° C. Yield 89 g (67%).

EXAMPLE 3

2,3,5-tri-O-benzyl-D-ribose[1]

10 g (23 moles) of 1-methyl-2,3,5-tri-O-benzyl-β-D-ribofuranoside are dissolved in 200 ml of dioxane and 50 ml of 1 N HCl are added to the solution. Boiling is then carried out for 3 hours under reflux and after cooling down the solution is neutralised with 1 N NaHCO₃ solution. Following this solvent is removed and the residue is taken up in 200 ml of CH₂Cl₂. The NaCl formed is filtered off and the solution is dried over Na₂SO₄. After removal of the solvent a yellow oil remains, which is added to a silica gel column and eluted with a mixture of chloroform and ether (70:30). R$_f$=0.59. A yellow oil is obtained. Yield: 9.0 g (93%).

EXAMPLE 4

1-hydrazino-2,3,5-tri-O-benzyl-D-ribose 18.1 g (43 mmoles) of 2,3,5-tri-O-benzyl-D-ribose are dissolved in 18 ml of absolute methanol and, while cooling and stirring 21.5 g (43.0 mmoles) of 100% hydrazine hydrate (dissolved in 20 ml of absolute methanol) are added to the solution. After a few minutes the ice bath is removed and stirring is carried out for 24 hours at room temperature. The excess hydrazine hydrate is drawn off (oil pump) together with the methanol in a rotary evaporator at room temperature. A viscous yellow oil remains which is dried further using an oil pump. Yield: 17.9 g (96%).

EXAMPLE 5

3,5-dimethyl-1-(2,3,5-tri-O-benzyl-D-ribofuranosyl)-pyrazole 6.7 g (15.4 mmoles) 1-hydrazino-2,3,5-tri-O-benzyl-D-ribose are dissolved in 10 ml of absolute ethanol. While stirring 1.54 g (15.4 mmoles) of acetylacetone (dissolved in 10 ml of absolute alcohol) are added to the solution. Yellow coloration occurs and the temperature rises slightly. Stirring is carried out for 24 hours at room temperature and, following this, the solvent is removed. A yellow oil is obtained, which is placed on a silica gel column and is eluted with ether. $R_f = 0,58$. A yellow oil is obtained. Yield: 5.55 g (72%).

EXAMPLE 6

3,5-dimethyl-1-($\beta$-D-ribofuranosyl) pyrazole 5.55 g (11.1 mmoles) of 3,5-dimethyl-1-(2,3,5-tri-O-benzyl-D-ribofuranosyl) pyrazole are dissolved in 25 ml of methanol. The solution is added to a suspension of 1 g of palladium in 25 ml of methanol. (The catalyst was pre-hydrogenated for this purpose for approximately 4 hours). To this mixture 0.8 ml of 12.5 n HCl is added so that the solution is 0.2 molar with respect to HCl. This mixture is hydrogenated at room temperature in a shaking device. After approximately 5 hours the hydrogenation is terminated. Hydrogen consumption: 900 ml (theoretically 740 ml). The solution is filtered off from the catalyst and added to an ion exchanger [Amberlite IRA-402 (OH$^-$ form)]. (Length 8 cm, diameter 1.5 cm). The eluate is reduced in volume, and yellowish crystals are obtained which are recrystallised from a little absolute ethanol. White crystals with a melting point of 160 to 162° C are obtained. Yield: 1.7 g (67%).

3,5-dimethyl-1-($\beta$-D-ribofuranosyl)pyrazole was converted in accordance with the method of Hampton[2] into the 2',3'-O-isopropylidene compound. From the NMR-spectrum it can be seen that in the case of 3,5-dimethyl-1-($\beta$-D-ribofuranosyl)pyrazole the -anomer is present.

EXAMPLE 7

3,5-diethyl-1-(2,3,5-tri-O-benzyl-D-ribofuranosyl)-pyrazole 3.9 g (9 mmoles) of 1-hydrazino-2,3,5-tri-O-benzyl-D-ribose are reacted with 1.41 g (9 mmoles) of heptane-dione-3,5 in a manner similar to the method of example 5. The oil produced is eluted on a silca gel column with a mixture of chloroform and ether (70:30). $R_f = 0.87$. Yield: 2 g (42.5%).

EXAMPLE 8

4-amino-1-(2,3,5-tri-O-benzyl-$\beta$-D-ribofuranosyl)-pyrazolo [3,4-d]pyrimidine 1.9 g (4.4 mmoles) of 1-hydrazino-2,3,5-tri-O-benzyl-D-ribose are dissolved in 10 ml of absolute methanol. To the solution 0.54 g (4.4 mmoles) of ethoxymethylenemalonodinitrile, dissolved in 10 ml of absolute methanol, are added dropwise. Slight heating occurs. Stirring is carried out at room temperature for 24 hours and following this for completion of the reaction refluxing is carried out for 30 minutes. Following this the product is separated by column chromatography. As an eluting agent use is made of a mixture of benzene and acetone (85:15). $R_f = 0.61$. A yellow oil is obtained which is boiled with 7 ml of orthoformic acid triethylester for 3 hours under reflux. (Bath temperature 160° C)[3]. After removal of the remaining ortho-ester the oil obtained is dissolved in 13 ml of ethanol. NH$_3$ is introduced into the solution at room temperature (for four hours). After removal of the ethanol purification is carried out by column chromatography (benzene to acetone = 50 to 50). $R_f = 0.58$. A yellow oil is obtained. Yield: 1.36 g (52%).

EXAMPLE 9

4-amino-1-($\beta$-D-ribofuranosyl)pyrazolo [3,4-d]pyrimidine 1.45 g (2.7 mmoles) of 4-amino-1-(2,3,5-tri-O-benzyl $\beta$-D-ribofuranosyl)pyrazolo [3,4-d]pyrimidine are hydrogenated in a manner similar to that of Example 6. The 4-amino-1-($\beta$-D-ribofuranosyl)pyrazolo [3,4-d]pyrimidine precipitates; however, during the reaction so that in this case the preparation is modified. The reaction mixture is filtered off (vacuum filter funnel) from the catalyst and the reaction product which has been partially precipitated. The obtained solution is neutralized with diluted NaHCO$_3$ solution. The catalyst with the remainder of the product is washed in a pointed funnel with the application of vacuum using hot water. The solution so obtained is neutralized and combined with the above solution. It is freed of solvent and the product, which is contaminated with a little NaCl, is recrystallised from H$_2$O. White needles are obtained. Yield: 350 mg (48%), Melting point: 253° C[4].

EXAMPLE 10

5-amino-4-carbethoxy-1-(2,3,5-tri-O-benzyl-D-ribofuranosyl)pyrazole 2.5 g (5.8 mmoles) of 1-hydrazino-2,3,5-tri-O-benzyl-D-ribose are dissolved in 10 ml of absolute ethanol. 0.98 g (5.8 mmoles) of ethoxymethylenecyanoacetic acid ethyl ester, dissolved in 10 ml of absolute ethanol is added to the solution. There is a slight increase in temperature and yellow discoloration. Stirring is carried out at room temperature for 24 hours. Following this boiling is carried out for 6 hours under reflux. The solvent is removed and purfication is carried out by column chromatography. Benzene and acetone (85:15). $R_f = 0.78$. A yellow oil is obtained. Yield: 2.7 g (84%).

EXAMPLE 11

1-(2,3,5-tri-O-benzyl-D-ribofuranosyl)-2-(p-nitro-benzylidene) hydrazine 2.4 g (5.55 mmoles) of 1-hydrazino-2,3,5-tri-O-benzyl-D-ribose are dissolved in 10 ml of absolute methanol. 0.84 g (5.55 mmoles) of p-nitrobenzaldehyde (dissolved in 8 ml of absolute methanol) are added to the solution. Stirring is carried out at room temperature and after approximately 5 minutes a yellow flaky precipitate appears. After 24 hours the precipitate is drawn off by suction and dried. Yield: 2.4 g (76%). Melting point: 93° C (from methanol).

EXAMPLE 12

5-amino-4-(N-formylcarbamoyl)-1-(2,3,5-tri-O-benzyl-D-ribofuranosyl) pyrazole 2 g (4.6 mmoles of 1-hydrazino-2,3,5-tri-O-benzyl-D-ribose are dissolved in 20 ml of absolute ethanol. 0.775 g (4.6 mmoles) of β-ethoxy-α-cyano-N-formylacryloamide are added while stirring to the solution. The solution immediately changes to a deep yellow color and β-ethoxy-α-cyano-N-formylacrylamide goes into solution. Stirring is carried out further at room temperature and small quantities of a yellow precipitate are formed. The reaction mixture is freed of ethanol and purified by column chromatography. Benzene and acetone (70:30). $R_f$ = 0.80. A yellow oil is obtained, which in accordance with the NMR-spectrum is 5-amino-4-(N-formylcarbamoyl)-1-(2,3,5 -trio-O-benzyl-D-ribofuranosyl)pyrazole. Yield: 1.8 g (69%).

EXAMPLE 13

4-hydroxy-1-(β-D-ribofuranosyl)pyrazole [3,4-d] pyramidine 2.5 g (5.8 mmoles) of 1-hydrazino-2,3-tri-O-benzyl-D-ribose are dissolved in 10 ml of absolute ethanol. While stirring 0.98 g (5.8 mmoles) of β-ethoxy-α-cyano-N-formylacryloamide (dissolved in 15 ml of hot absolute ethanol) are added to the solution. A deep yellow colouration is produced. After 24 hours ethanol is removed and a viscous yellow oil [5-amino-4-(N-formylcarbamoyl)-1-(2,3,5-tri-O-benzyl-D-ribofuranosyl)pyrazole] is obtained which in this case was not further purified. The oil is now heated for 40 minutes to 150° C[5], and a dark viscous oil is produced. Separation by column chromatography (benzene and acetone = 55:45) yields 4-hydroxy-1-(2,3,5-tri-O-benzyl-β-D-ribofuranosyl)-pyrazolo[3,4-d]pyrimidine. $R_f$ = 0,64.

Removal of the protective groups is carried out in accordance with the method of Example 6. A glass-like product is obtained which, by taking up in diethylether, crystallises. White crystal (from acetonitrile) Melting point = 204°C.

Example 14

2,3,4,6-tetra-O-benzyl-D-glucose 20 g (36.1 mmoles) of 1-methyl-2,3,4,6-tetra-O-benzyl-α-D-glycopyranoside (dissolved in 400 ml of dioxane) are boiled after the addition of 200 ml of half-concentrated hydrochloric acid for 24 hours at 105°to 110° C. Then the reaction mixture is allowed to cool. A dark brown clear solution is produced which is neutralised by the addition of solid sodium hydrogen carbonate. Following this the volatile components are drawn off on a rotary evaporator. The remainng brown residue is extracted with 3 150 ml portions of boiling methylene chloride. The solvent is drawn off and the remaining sirup (oervaded with crystals) is dissolved in boiling methanol. From this solutions the desired product precipitates out in the form of acicular crystals. On reducing the bulk of the mother liquor, a further fraction is obtained. For purification both fractions are again recrystallised from methanol. On carrying out the full reduction in bulk of the mother liquor 8 to 10 g of the starting compound are reobtained in the form of a brown sirup. Yield: 6.8 g (35%). Melting point 151° C. 1-methyl-α-D-glucopyranoside was prepared in accordance with the method of HELFERICH and SCHAFER [6]; 1-methyl-2,3,4,6-tetra-O-benzyl-α-D-glucopyranoside, in accordance with TATE and BISHOP [7].

EXAMPLE 15

1-hydrazino-2,3,4,6-tetra-O-benzl-D-glucose 1.77 g (55.5 mmoles) of anyhdrous hydrazine (which has been twice distilled over NaOH) are dissolved in 3 ml of absolute methanol and the solution is cooled in an ice bath. While stirring 3.0 g (5.55 mmoles) of 2,3,4,6-tetra-O-benzyl-D-glucose dissolved in 15 ml of absolute tetra-hydrofuran were added dropwise. After a few minutes the ice bath is removed and the solution is heated to 50° C. At this temperature the mixture is stirred for 7 days in closed flasks. Following this the excess hydrazine is drawn off with the solvent at room temperature in a rotary evaporator. For removal of the last traces of hydrazine the substance is dried for 48 hours with an oil pump running. A colorless viscous sirup remained, yield: 3.05 g (100%).

EXAMPLE 16

3,5-dimethyl-1-(2,3,4,6-tetra-O-benzyl-β-D-glucopyranosyl)pyrazole 3.05 g (55.5 mmoles) of 1-hydrazino-2,3,4,6-tetra-O-benzyl-D-glucose are dissolved in 15 ml of absolute tetrahydrofuran (THF). To this 550 mg (5.5 mmoles) of acetylacetone are added (dissolved in 5 ml of absolute THF) and the mixture is stirred in a closed flask at room temperature. The reaction mixture gradually takes on a lemon-yellow coloration. After 4 hours the reaction is interrupted by drawings off the solvent at room temperature. A yellow sirup is obtained, which is separated by column chromatography (silica gel and ether). The reaction product is obtained as a yellow oil, yields: 1.8 g (53%); $R_f$ (silica gel to ether): 0.92.

EXAMPLE 17

3,5-dimethyl-1-(β-D-glucopyranoxyl)pyrazole

For the hydrogenating debenzylation of 3,5-dimethyl-1-(2,3,4,6,-tetra-O-benzyl-β-D-glucopyranosoyl)-pyrazole te method of GLAUDEMANS and FLETCHER [8] was employed in a modified form. 1 g of palladium black is pre-hydrogenated in 25 ml of absolute tetrahydrofuran (THF) 4 hours in a shaking appartus. Then a solution of 1.8 g (2.9 mmoles) of 3,5-dimethyl-1-(2',3',4',6'-tetra-O-benzyl-β-D-glucopyranoxyl)pyrazole in 25 ml of absolute THF and 0.8 ml of 12.5 N hydrochloric acid are added so that the solution in all is 0.2 molar with respect to hydrochloric acid. This mixture is hydrogenated for 24 hours at room temperature.

$H_2$ uptake calculated: 290 ml
$H_2$ uptake found: 285 ml

Then the catalyst was filtered off and the practically colorless solution produced was run over a column with the anion exchanger Amberlite IRA-402 in the OH⁻ form and elated with methanol. After the removal of the solvent a white amorphous sticky mass remained. This mass is dissolved in the necessary quantity of boiling ethanol and allowed to stand for several days in a refrigerator for crystallisation. The desired product is obtained in the form of a white crystalline powder.

For analysis recrystallisation is carried out twice again from absolute acetone nitrile. Yield: 350 mg (48%), Melting point: 147° and 148° C (after preceding sintering) $[\alpha]^{22}_{365} = 50.9°$ in methanol (C = 10.4 mg/ml).

EXAMPLE 18

3,5-dimethyl-1-(4,6-Oisopropylidene-β-D-glucopyranosyl) pyrazole

For preparation the method given by EVANS et al.[9] was employed in a modified form.

100 mg (0.39 mmole) of 3,5-dimethyl-1-(β-D-glucopyranosyl)pyrazole are dissolved in 15 ml of absolute acetene. To this there are added 405 mg (3.5 mmoles) 2,2-dimethoxypropane and then 405 mg (1.2 mmoles) of bis-(p-nitrophenyl)-phosphoric acid are added as a catalyst and the mixture is stirred at room temperaure for 5 hours. During the course of the reaction the solution assuems a yellow to yellow-brown color. After the end of the reaction neutralisation is carried out by the addition on 20 ml of 0.1 molar sodium hydrogen carbonate solution. Then the volatile components are drawn off on a rotary evaporator. The remaining yellow residue is extracted with 3 20 ml portions of boiling chloroform. After removal of the chloroform a coloreless oil remains, which is purified by column chromatography (silica gel/acetone). Again a colorless oil is obtained. Yield: 105 mg (90%), $R_f$ (silica gel/actone): 0.67.

EXAMPLE 19

N-[2,2-dicyanoethenyl-(1)]-N'-(2,3,4,6-tetra-O-benzyl-D-glucopyranosyl) hydrazine 3.05 g (5.55 mmoles) of 1-hydrazino-2,3,4,6-tetra-O-benzyl-D-glucose are dissolved in 10 ml of absolute tetra-hydrofuran (THF). To this solution of 675 mg (5.55 mmoles) of ethoxymethylenemalodinitrile are added in 5 ml of absolute THF. The reaction mixture immediately assumes the yellow color of the ethoxymethylenemalodinitrile. The solution is stirred for 5 hours at room temperature and then the solvent is removed. The remaining brown-yellow vary viscous and practially glass-like sirup is separated by column chromatography (silica gel/ether). 2.2 g of a red oil, which is caused to crystallise by taking up in methanol are obtained. The desire product is obtained in the form of a white finely crystallised powder. Yield: 2.0 g (59%), melting point: 105° and 106° C (sintered at 75° C), $R_f$ (silica gel/ether); 0.55.

Example 20

4-cyano-5-amino-1-(2,3,4,6-tetra-O-benzyl-D-glucopyranosyl)pyrazole 200 mg (0.31 mmoles) of N-[2,2-dicyanoethenyl-(1)]-N'(2',3',4',6'-tetra-O-benzyl-D-glucopyranosyl)-hydrazine are heated in an open test tube for 90 minutes in substance at 120° C. As a result a yellow glass-like product is produced which is dissolved while hot in a mixure of cyclohexane and $CCl_4$(50:50). From this solution the product precipitates in the form of a jelly-like voluminous precipitate. After vacuum filtration the powder obtained is dried for removal of the solvent for several days under an oil pump vacuum.

Yield: 180 mg (90%); melting point: 144° C; $R_f$ (silica gel/ether): 0.63.

EXAMPLE 21

1-hydrazino-5-0-trityl-D-ribofuranoside 4.16 g (10 mmoles) of 5-O-trityl-D-ribofuranose dissolved in 12 ml of abosolute tetrahydrofuran (THF) is added dropwise while stirring and cooling in an ice bath to a solution of 0.64 g (20 mmoles) of anhydrous hydrazine in 2 ml of absolute methanol. After a few minutes the ice bath is removed and the solution is stirred for 3 hours at room temperature. Then the solvent together with the express hydrazine is removed at room temperature in a rotary evaporator and the residue is freed of traces of solvent and hydrazine by holding in an oil pump vaccum for 2 days. A white foam is produced which can be broken up to provide a sticky powder. Yield: 4.0 g (99 %).

5-O-trityl-α-D-ribofuranose was produced by the method of BREDERECK et al.[10].

EXAMPLE 22

3,5-dimethyl-1-(5-O-trityl-α-D-ribofuranosyl)pyrazole

To a solution of 4.0 g (10 mmoles) of 1-hydrazino-5-O-trityl-D-ribofuranoside in 20 ml of absolute tetrahydrofuran (THF) 1.0 g (10 mmoles) of acetylacetone (dissolved in 5 ml of absolute THF) is added. The solution immediately takes on a deep yellow color. The reaction mixture is stirred up 4 hours at room temperature. Then the solvent is removed. A yellow stick amorphous powder which is separated by colum chromatography (silica gel/ether) is obtained. After thorough drying, an oil pump vacuum white foam was produced. Yield: 1.5 g (32%); $R_f$ (silica gel/ether 0.53.

3,5-dimethyl-1-(β-D-ribofuranosyl)pyrazole

For splitting off the trityl group, in essence the method given by BREDERECK et al.[11] was carried out. 1.5 g (3.2 mmoles) of 3,5-dimethyl-1-(5' trityl-β-D-ribofuranosyl)pyrazole are dissolved in 15 ml of 80% acetic acid and stirred for 10 minutes while being boiled under reflux. On cooling down the red solution, a white precipitate of triphenylcarbinol is produced. After the addition of 20 ml of water, the precipitate is filtered off and the filtrate, for neutralisation, is run over a column with an ion exchanger Amberlite IRA-402 in the $OH^{116}$ form and the substance is eluted with methanol. After removal of the solvent from the yellow solution produced, the remaining yellow sirup is mixed for crystallisation with a few drops of 99% ethanol and allowed to stand for 24 hours at room temperature. Slightly yellow compact crystals are produced which are recrystallised for purification from absolute acetonenitrile. Yield: 480 mg (66%), melting point: 162° and 163° C; $[\alpha]$ $578^{22} = 97.2°$ in methanol (C = 17.1 mg/ml).

EXAMPLE 24

3,5-dimethyl-1-(2,30-isopropylidene-β-D-ribofuranosyl)-pyrazole

For preparation, the method given by HAMPTON[2] was used. 170 mg (0.75 mmole) of 3,5-dimethyl-1-(β-D-ribofuranosyl)-pyrazole are dissolved in 20 ml of absolute acetone. Then 780 mg (1 mmole) of bis-(p-nitrophenyl)phosphoric acid are added and the mixture is stirred for 4 hours at room temperature in a closed flask. Following this, neutralisation is carried out by the addition of 15 ml of 0.1 N aqueous sodium hydrogen carbonate solution. The volatile components are drawn off using a rotary evaporator. The yellow residue is extracted with 5 20 ml portions of boiling chloroform. After the removal of the chloroform a practically colorless sirup, which is purified by column chromatography (silica gel/ether) remains. A colorless sirup is again produced. Yield: 190 mg (95 %); $R_f$ (silica gel/ether): 0.6.

EXAMPLE 25

2,3-O-isopropylidene-D-ribose 14.6 g (97.5 mmoles) of D-ribose and 10.5 g (105 mmoles) of isopropenyl acetate are introduced into 100 ml of dry acetone. While stirring, 0.3 g of red $H_gO$ and 0.3 ml of $BF_3$-etherate are added. Stirring is carried out for 5 hours at room temperature. As a result the D-ribose and also the HgO slowly go into solution and furthermore heating occurs. The reaction mixture is carefully poured into 100 ml of saturated $NaHCO_3$-solution. The remaining acetone and the water and separated by rotation and the remaining mass is extracted 4 times with respective 50 ml portions of hot acetone. Following this the acetone is removed. The remaining colorless oil usually contains traces of mercury salts, and filtration over silica gel (small dropping funnel) is recommended. As a solvent ether is used. The product so obtained is sufficiently purified for further reactions (for fine purification, distillation or column chromatography with ether is recommended). Raw yield: 12 g (68%).

EXAMPLE 26

1-hydrazino-2,3-O-isopropylidene-D-ribose 3.6 g (19 mmoles) of 2,3-isopropylidene-D-ribose are dissolved in 20 ml of absolute methanol. While stirring, 9.5 g (190 mmoles) of 100 percent hydrazine hydrate, dissolved in 15 ml of absolute methanol, are added. Stirring is now carried out for 2 days at room temperature and then a rotary evaporator is used with an oil pump vacuum at room temperature to remove methanol and superfluous hydrazine hydrate. The oil so obtained is taken up a further 2 times with two respective 20 ml portions of methanol and then freed of methanol under to above conditions. The obtained colorless sirup is dried for one further day under oil pump vacuum. Yield: 3.8 g (94%).

EXAMPLE 27

1-hydrazino-2,3,5-tri-O-methyl-D-ribose 1.7 g (8.5 mmoles) of 2,3,5-tri-O-methyl-D-ribose are dissolved in 5 ml of absolute methanol. While stirring, 4.25 g (85 mmoles) of 100% hydrazine hydrate (dissolved in 5 ml of absolute methanol) are added. As a result slight heating occurs. Stirring is carried out for 2 days of room temperature. Following this methanol and superfluous hydrazine hydrate are removed in a rotary evaporator at room temperature (oil pump vacuum). Following this drying is carried out for one day under oil pump vacuum. A colorless oil is obtained. Yield: 1.6 g (92 %).

EXAMPLE 28

1-(2,3-O-isopropylidene-$\beta$-D-ribofuranosyl)pyrazole 1.4 g (6.9 mmoles) of 1-hydrazino-2,3-O-isopropylidene-D-ribose are dissolved in 25 ml of absolute methanol. While stirring, 0.92 g (6.9 mmoles) of 75% 2-ethoxyacrolein are added to the solution. A deep yellow coloration is immediately produced. After stirring for 26 hours at room temperature, the solution is boiled for 1 day under reflux. Following this the solvent is removed and thus-produced yellow oil is separated by column chromatography. Chromatography is first carried out with ether/acetone (95 v/5 v) and then with ether/chloroform (90 v/10 v), in which case the second fraction is to be processed here (substance made visible in iodine chamber). Yield: 500 mg (30%).

EXAMPLE 29

3,5-dimethyl-1-(2,3-O-isopropylidene-$\beta$-D-ribofuranoxyl)pyrazole a. 700 mg (3.45 mmoles) of 1-hydrazino-2,3-O-isopropylidene-D-ribose are dissolved in 4 ml of absolute methanol. While stirring, 345 mg (3.45 mmoles) of acetylacetone are added, which is dissolved in 3 ml of absolute methanol. Yellow coloration and slight heating immediately occur. Stirring is carried out for 24 hours at room temperature and, following this the solvent is removed. The obtained yellow oil is separated by column chromatography. As an eluating medium use is made of ether (substance made visible in iodine chamber). A colorless oil is obtained. Yield: 700 g (75%).

b. 456 mg (2 mmoles) of 3,5-dimethyl-1-($\beta$-D-ribofuranoxyl)-pyrazole and 1728 mg (16 mmoles) of 2,2-dimethoxypropane are placed in 25 ml of dry acetone. While vigorously stirring, 1360 mg (4 mmoles) of bis-(4-nitrophenyl) phosphate are added to the suspension. Stirring is now carried out at room temperature. After a short time the nucleoside has added in the solution. The reaction mixture is, however, very turbid. After 22 hours a clear solution is obtained and this is diluted with 28 ml of water. The solution is now poured onto an ion exchanger column (length 8 cm, diameter 1.5 cm). As an ion exchanger resin use is made of AMBERLITE IRA-402 in the $OH^-$-form. The exchanger is rinsed with acetone/water (1 v/1 v) and the combined solutions are subjected to evaporation by means of a rotation evaporator (hereinafter: rotation). The yellowish oil is purified by column chromatography. Eluation is carried out with ether (substance made visible in iodine chamber). A colorless oil is obtained. Yield: 400 mg (75%).

The chromatographic behaviour and the NMR-spectroscopic data of the substances produced in accordance with (a) and (b) are identical.

EXAMPLE 30

3,5-dimethyl-1-(2,3,5-tri-O-methyl-$\beta$-D-ribofuranosyl)pyrazole a. 1.5 g (7.3 mmoles) of 1-hydrazino-2,3,5-tri-O-methyl-D-ribose are dissolved in 4 ml of absolute methanol. While stirring, 0.73 g (7.3 mmoles) of acetylacetone (dissolved in 5 ml of absolute methanol) are added. Yellow coloration and slight heating immediately occur. Stirring is carried out for 1 day at room temperature and then the solvent is removed. A yellow oil is obtained in which a few crystals (3,5-dimethylpyrazole) are present. Ether is used as an eluating agent (substance made visible in the iodine chamber). A colorless highly mobile oil is obtained. Yield: 810 mg (41%).

b. 632 mg (2.77 mmoles) of 3,5-dimethyl-1-($\beta$-D-ribofuranosyl])-pyrazole are stirred into 1 ml of 40% sodium hydroxide solution. Then 315 mg (2.5 mmoles)

of distilled dimethyl sulfate are added. Stirring is now carried out at 60° C. After 2.5 hours a further portion of 315 mg (2.5 mmoles) of distilled dimethyl sulfate are added to the reaction mixture. Stirring is now carried out for 2.5 hours at 60° C and then the mixture is heated for 10 minutes at 100° C. Following this the reaction mixture is cooled to 0° C and then extracted with ether. Purification is carried out as in the first method by chromatographic purification using ether. Yield: 400 mg (54%).

The chromatographic behaviour and the NMR-spectroscopic data of the substances produced in accordance with (a) and (b) are identical.

EXAMPLE 31

3,5-dimethyl-1-(β-D-ribofuranosyl)pyrazole 1.2 g (4.5 mmoles) of 3,5-dimethyl-1-(2,3-O-isopropylidene-β-D-ribofuranosyl)pyrazole and 2 g AMBERLITE IR 120 (H⁺-form) are placed in 20 ml of an acetone/water (3 v/1 v) mixture. Stirring is now carried out for 4 hours at 40° C. Following this the ion exchanger is filtered off. The ion exchanger is washed with water and then with aqueous $NH_3$. The purified solutions are then subjected to rotation to produce an oil that, on treating with ether, becomes solid. The solid is recrystallized from acetonitrile. Melting point: 160 to 162° C. Yield: 450 mg (54%)

EXAMPLE 32

3,5-diethyl-1-(2,3-O-isopropylidene-β-D-ribofuranosyl)-pyrazole 1.6 g (7.9 mmoles) of 1-hydrazino-2,3-O-isopropylidene-D-ribose are dissolved in 25 ml of absolute methanol. While stirring, 1.23 g (7.9 mmoles) of heptanedione-3,5 are added. Yellow coloration gradually occurs. After 2 days of stirring at room temperature, the solvent is drawn off and a yellowish oil (which is purified by column chromatography) is obtained. Ether is used as an eluting agent. In order to be able to obtain the product in an analytically pure condition, further chromatography with chloroform as an eluating agent is recommended (substance made visible in the iodine chamber). A colorless oil is obtained. Yield: 1.44 g (48 %).

EXAMPLE 33

3,5-diethyl-1-(β-D-ribofuranosyl)pyrazole (a) 1.5 g (2.85 mmoles) of
3,5-diethyl-1-(2,3,5-tri-O-benzyl-β-D-ribofuranosyl)-pyrazole are hydrogenated in a manner similar to that of Example 6. After preparation a yellowish oil is obtained which is purified by column chromatography. This process is repeated twice. As an eluating agent use is made of solvent mixtures of (a) acetone/ether (70 v/ 30v) and (b) chloroform/methanol (90 v/10 v) (substance made visible in the iodine chamber). A thick colorless oil is obtained. Yield: 250 mg (38%).

b. 650 mg (2.2 mmoles) of 3,5-diethyl-1-(2,3-O-isopropylidene-β-D-ribofuranosyl)pyrazole are dissolved in a mixture of 10 of methanol and 10 ml of 2 N HCl and stirred at 60° C for 20 minutes. Accordingly, a thin layer chromatogram can be used to show that there is no more starting material present. Neutralisation is carried out with $NaHCO_3$, and the solvent is removed. The obtained residue is extracted with acetone. The acetone is drawn off and the remaining yellow oil is purified twice by column chromatography. As eluating agents use is made of solvent mixtures of (a) acetone/ether (70 v/30 v) and (b) chloroform/methanol (90 v/10 v) substance made visible in the iodine chamber). Yield: 310 mg (53%).

The chromatographic and NMR-spectroscopic behaviour of the substances prepared in accordance with (a) and (b) is identical.

EXAMPLE 34

3,5-diphenyl-1-(2,3-O-isopropylidene-β-D-ribofuranosyl)-pyrazole 1.2 g (5.9 mmoles) of 1-hydrazino-2,3-O-isopropylidene-D-ribose are dissolved in 25 ml of absolute methanol. While stirring, 1.32 g (5.9 mmoles) of dibenzoylmethane are added. Stirring is then carried out for 2 days at room temperature. At the end of this time it can be shown by a thin layer chromatogram that no formation of the nucleoside has occurred and instead 3,5-diphenylpyrazole has been formed. The reaction mixture is now boiled for 2 days under reflux and, following this, a thin layer chromatogram shows a new spot. The reaction mixture is freed of methanol and purified by column chromatography. Eluation is carried out with ether/chloroform (70 v/30 v). One obtains an impure fraction in which in accordance with the NMR-spectrum the compound 3,5-diphenyl-1-(2,3-O-isopropylidene-β-D-ribofuranosyl)pyrazole is contained. Raw yield: 150 mg (approximately 4%).

EXAMPLE 35

5-amino-4-cyano-1-(2,3-O-isopropylidene-β-D-ribofuranosyl)-pyrazole 2.4 g (11.8 mmoles) of 1-hydrazino-2,3-O-isopropyliden e-D-ribose are dissolved in 30 ml of absolute methanol. While stirring, 1.44 g (11.8 mmoles) of ethoxymethylene-malondinitrile are added. Solution and yellow coloration immediately occur. Stirring is now carried out for 17 hours at room temperature and, following this, boiling is carried out for a further 6 hours under reflux. Following this, the solvent is removed by rotation. The yellow oil so obtained is separated 2 times by column chromatography. Following this, ether eluation is carried out which is followed by eluation of the mixture of ether and benzene (90 v/10 v). A white foamy product is obtained. Yield: 1.7 g (52%).

EXAMPLE 36

5-amino-4-cyano-1-(β-D-ribofuranosyl)pyrazole 0.9 g (3.22 mmoles) of 5-amino-4-cyano-1-(2,3-O-isopropylidene-β-D-ribofuranosyl)pyrazole are dissolved in 20 ml of a mixture of acetone/water (3 v/1 v). To the solution 2 g of AMBERLITE IR-120 (H⁺-form) are added. After this it can be seen by a thin layer chromatogram that the starting compound has, to a large extent, been reacted. The ion exchanger is now removed and washing is carried out with water and then with hot $NH_3$ water. The purified aqueous solutions are subjected to rotation. The product so obtained is treated with ether, and a yellow solid is obtained. Recrystallisation is carried out twice from approximately 10 ml of water. White needles, which have a melting point of 219° C, are obtained. Yield: 590 mg (76%).

EXAMPLE 37

5-amino-4-carbethoxy-1-(2,3-O-isopropylidene-β-D-ribofuranosyl)pyrazole 1.4 g (6.9 mmoles) of 1-hydrazino-2,3-isopropylidene-β-D-ribose are dissolved in 25 ml of absolute methanol. While stirring, 1.16 g (6.9 mmoles) of ethyl ethoxymethylenecyanoacetate are added. Rapid solution and simultaneous yellow coloration occur. Stirring is carried out for 2 days at room temperature, and then boiling is carried out for 1 day under reflux. Following this, the solvent is removed and a yellow oil is obtained which is purified by column chromatography. As an eluating agent use is made of ether. One obtains a white foamy product. Yield: 1.1 g (49%).

EXAMPLE 38

5-amino-4-carbethoxy-1-(β-D-ribofuranosyl)pyrazole 1.1 g (3.37 mmoles) of 5-amino-4-carbethoxy-1-(2,3-O-isopropylidene-β-D-ribofuranosyl)pyrazole are dissolved in 5 ml of methanol. 20 ml of 1 N HCl are added to the solution. The resulting turbid solution is stirred for 25 minutes at 60° C. In accordance with a thin layer chromatogram after this time no more starting product can be shown to be present. The solution is neutralised with solid NaHCO$_3$ and freed of solvent. The residue is extracted with acetone in order to separate it form NaCl. The combined acetone solutions are subjected to rotation and a yellow solid is obtained. For recrystallisation a substance is dissolved in little acetone, and benzene is added dropwise until crystallisation begins. A white product is obtained which holds the benzene extraordinarily strongly. In order to remove the benzene, drying is carried out over paraffin for 2 days at 90° C with a continuous oil pump vacuum. Melting point: 101° C. Yield: 650 mg (67%).

EXAMPLE 39

5-amino-4-(N-formylcarbamoyl)-1-(2,3-O-isopropylidene-β-D-ribofuranosyl)pyrazole 2.1 g (10.3 mmoles) of 1-hydrazine-2,3-O-isopropylidene-D-ribose are dissolved in 30 ml of absolute methanol. While stirring, 1.8 g (10.7 mmoles) of 2-ethoxy-1-cyano-N-formylacrylamide are added. Immediate solution and simultaneous strong yellow coloration occur. Stirring is carried out for 1 day at room temperature and then the mixture is boiled for 6 hours under reflux. Then the precipitate formed is removed by vacuum filtration and the solvent is removed. The tough yellow material obtained is then purified by column chromatography using benzene/acetone (40 v/60 v) as an eluating agent. As the first fraction one obtains the desired product in a further fraction approximately 500 mg of highly impure 1-(2,3-o-isopropylidene-β-D-ribofuranosyl)-4-hydroxy-pyrazolo-[3,4-d]pyrimidine can be obtained. This chromatographic purification is sufficient for further reaction. In order to obtain an analytically pure product, further column chromatographic purification with benzene/acetone (85 v/15 v) as an eluating agent is recommended. In this manner it is possible to obtain a white foamy product which is dissolved in a very small quantity of CH$_2$Cl$_2$. While cooling with ice, a few crystals of 5-amino-4-carbamoyl-1-(2,3-0-isopropylidene-β-D-ribofuranosyl)-pyrazole are added. After some time a crystalline mass is formed which is vacuum filtered and recrystallised from chloroform. The product crystallises out in white needles. After drying in an oven at 0° C, the compound still contains one-four mole of chloroform. Drying at a higher temperature is not possible since the product then becomes partly converted into 5-amino-4-carbamoyl-1-carbamoyl-1-(2,3-O-isopropylidene-β-D-ribofuranosyl)pyrazole and 1-(2,3-O-isopropylidene-β-D-ribofuranosyl)-4-hydroxypyrazolo-[3,4-d-]pyrimidine. Melting point: between 70° and 75° C (decomposition). Yield: 900 mg (24%).

EXAMPLE 40

5-amino-4-(benzoylcarbamoyl)-1-(2,3-O-isopropylidene-β-D-ribofuranosyl)pyrazole 1.8 g (8.8 mmoles) of 1-hydrazino-2,3-O-isopropylidene-D-ribose (1.2 fold excess) are dissolved in 200 ml of absolute tetrahydrofuran (THF). White stirring, 1.82 g (7.35 mmoles) of 2-ethoxy-1-cyano-N-benzoylacryloamide (which, have been previously dissolved in 25 ml of absolute THF are added. Deep yellow coloration and simultaneous cloudiness of the solution occur. Furthermore, a slight heating is detected. Stirring is now carried out for 1 day at room temperature, and then formed precipitate is filtered off. The filtrate is freed of THF and a yellow tough product is obtained which is purified by column chromatography. As an eluating agent use is made of a mixture of chloroform/methanol (80 v/10 v). The foamy product so obtained is sufficiently purified for further reactions. In order to obtain an analytically pure product, recrystallisation from chloroform is recommended. In this manner it is possible to obtain white crystals which hold the chloroform very strongly. In order to remove the chloroform, drying is carried out for 1 day at 100° C over paraffin with a continuously running oil pump. Melting point: 160° to 161° C. Raw yield: 1.5 g (51%).

EXAMPLE 41

5-amino-4-carbamoyl-1-(2,3-O-isopropylidene-β-D-ribofuranosyl)pyrazole a. 326 mg (mmole) of 5-amino-4-(N-formylcarbamoyl)-1-(2,3-O-isopropylidene-β-D-ribofuranosyl)pyrazole are dissolved in 10 ml of absolute methanol. A little bis-(p-nitrophenyl)phosphoric acid is added. The solution so obtained is heated for 30 minutes under reflux. Following this, no more starting material can be detected by a thin layer chromatogram. The solvent is removed. The product so obtained, which is still contaminated with catalyst, can be recrystallised from chloroform with the addition of a little benzene. White needles with a melting point of 181° C are obtained.

Yield: 200 mg (67%). b. 1.5 g (3.7 mmoles) of 5-amino-4-(benzoylcarbamoyl)-1-(2,3-O-isopropylidene-β-D-ribofuranosyl)pyrazole are dissolved in 40 ml of absolute methanol. 270 mg (5 mmoles) of sodium methylate are added. The solution is now boiled for 45 minutes under reflux. Following this, neutralisation is carried out with 0.5 N HCl and then methanol and water are removed. The residue is extracted with acetone and the desired product and also the methyl benzoate occurring as a reaction product are found in the acetone phase. In order to undertake separation from the ester, the acetone is first removed and then the residue is taken up with 100 ml of $H_2O$. In order to obtain complete dissolving, boiling is carried out for a short time. After cooling, the product is shaken up twice with respective 50 ml portions of low boiling point petroleum ether. Following this, the aqueous phase is subjected to rotation. The solid produce so obtained is recrystallised from chloroform with the addition of a little benzene. White needles with a melting point of 181° C are obtained. Yield: 800 mg (72%).

The two products produced in accordance with methods (a) and (b) are identical as regards their mixed melting points, and their chromatographic and NMR-spectroscopic properties.

EXAMPLE 42

1-(2,3-O-isopropylidene-β-D-ribofuranosyl)-4-hydroxypyrazolo-[3,4-d]-pyrimidine 298 mg (1 mmole) of 5-amino-4-carbamoyl-1-(2,3-O-isopropylideneβ-D-ribofuranosyl)pyrazole are dissolved in 5 ml of triethyl orthoformate and heated for 100 minutes at 140° C. Following this 10 ml of absolute ethanol are added to the cooled reaction mixture, 100 mg (4 mmoles) of sodium having previously between dissolved in the ethanol. This mixture is stirred for 3 hours at 80° C and, following this, it can be seen from a thin layer chromatogram that the formation of 1-(2,3-O-isopropylidene-β-D-ribofuranosyl)-4-hydroxypyrazolo-[3,4-d]-pyrimidine has occurred. Neutralisation is carried out with 0.5 N HCl and solvent is removed in a rotary evaporator. As a residue there remains a yellow oil, which is purified by column chromatography. As an eluating agent use is made of a mixture of benzene/acetone (40 v/60 c) and for following fine purification use is made of a mixture of chloroform/methanol (90 v/10 v). A white foamy product is obtained. Yield: 200 mg (65%).

EXAMPLE 43

5',2-anhydro-[3,5-dimethyl]-1-(2,3-O-isopropylidene-β-D-ribofuranosyl)pyrazolium]-p-toluene sulfonate 900 mg (3.35 mmoles) of 3,5-dimethyl-1-(2,3-O-isopropylidene-β-D-ribofuranosyl)pyrazole are dissolved in 20 ml of dry pyridine and cooled down to 0° C. While stirring, 890 mg (4.7 mmoles) of tosyl chloride (1.4 fold excess) are added. Stirring is now carried out for 18 hours at 0° C and, following this, the pyridine is removed in a rotary evaporator at room temperature (oil pump vacuum). As a residue a whitish greasy mass is obtained which is shaken up with absolute ether in order to separate off pyridine hydrochlorie. The etheric solution, which contains the remaining tosyl chloride, unreacted 3,5-dimethyl-1-(2,3-O-isopropylidene-β-D-ribofuranosyl)pyrazole and the nucleoside tosylated in the 5-position, is subjected to rotation. A colorless thick and turbid oil is obtained. Raw yield: approximately 1 g.

This product is now purified by column chromatography. As an eluating agent use is made of a mixture of $CCl_4$ and ether (50 v/50 v). In the case of this chromatography the major part of the 5'-tosylnucleoside goes into the cyclonucleoside 5',2-anhydro-[3,5-dimethyl-1-(2,3-O-isopropylidene-β-D-ribofuranosyl)pyrazolium]-p-toluene sulfonate, which can no longer be eluated from a silica gel column. One obtains a small fraction of colorless very tough material. Final yield: 150 mg (10%).

EXAMPLE 44

5-amino-3-methyl-1-(2,3-O-isopropylidene-β-D-ribofuranosyl)-1,2,4-triazole 1.3 g (6.4 mmoles) of 1-hydrazino-2,3-O-isopropylidene-D-ribose are dissolved in 30 ml of absolute tetrahydrofuran and the mobile turbid solution is cooled down to 0° C. While stirring and during a period of 1 hour a solution of 0.72 g (6.4 mmoles) of ethyl N-cyano-ethanimidate is added dropwise. Stirring is continued further and the ice bath is allowed to heat up slowly to room temperature. After 18 hours a yellow solution is obtained which is boiled for a further 3 hours under reflux. Following this the solvent is removed. An oily product remains which may take on a strong red coloration. This product is now separated several times by column chromatography. Eluation is first carried out with chloroform/methanol (80 v/10 v). The middle fraction mixture is further prepared. Eluation is now carried out with benzene/acetone (25 v/75 v) and a relatively pure product is obtained (NMR-spectrum). For complete purification further separation is recommended. As an eluating agent use is made of acetone. A colorless oil is obtained which, in the present case, forms a few crystals. For this reason recrystallisation from chloroform with the addition of benzene is carried out in order to produce white crystals. Melting point: 141° C. Yield: 260 mg (15%).

EXAMPLE 45

1-hydrazino-2,3,5-tri-O-benzyl-D-arabinose

To a solution of 3.8 g (119 mmoles) of anhydrous hydrazine in 10 ml of absolute methanol a solution of 5 g (11.9 mmoles) of 2,3,5-tri-O-benzyl-D-arabinose in 10 ml of absolute tetrahydrofuran (THF) is added dropwise while stirring and cooling in an ice bath at a moderate speed. After 10 minutes the ice bath is removed and the solution is stirred for 6 hours at room temperature. Then the solvent is removed with the superfluous hydrazine, and the remaining yellowish oil is dried for removal of the last traces of hydrazine for one day under a continuous oil pump vacuum. 2,3,5-tri-O-benzyl-D-arabinose is produced in accordance with the method given by TEJINA and FLETCHER[12].

EXAMPLE 46

3,5-dimethyl-1-(2,3,5-tri-O-benzyl-$\beta$-D-arabinofuranosyl)-pyrazole

To a solution of 5.1 g (11.9 mmoles) of 1-hydrazino-2,3,5-tri-O-benzyl-D-arabinose in 10 ml of absolute ethanol 1.19 g (11.9 mmoles) of acetylacetone, also dissolved in 10 ml of absolute ethanol, are added. The solution is initially somewhat turbid and heats up appreciably, but then becomes clear later. Then the solvent is drawn off. A yellow oil remains which is separated by column chromatography (silica gel, benzene-acetone 95:5). Yield: 3.8 g (64%); $R_f$ (silica gel, benzene-acetone 95:5): 0.4.

EXAMPLE 47

3,5-dimethyl-1-($\alpha$-D-arabinofuranosyl)pyrazole 1 g of Pd-black is pre-hydrogenated for 2 hours in 25 ml of absolute methanol. Then 3 g (6.0 mmoles) of 3,5-dimethyl-1-(2,3,5-tri-O-benzyl-$\alpha$-D-arabinofuranosyl)pyrazole are added in 25 ml of absolute methanol and 0.8 ml of concentrated hydrochloric acid. Hydrogenation is carried out for 20 hours at room temperature. Then the catalyst is filtered off and the reaction mixture is fed onto a column with 20 g of amberlite IRA-402 in the OH$^-$-form for neutralisation and is eluated with methanol. After drawing off the solvent, a colorless syrup (which cannot be used for crystallization) remains. For purification therefore the substance is only dissolved in methanol and boiled up with active charcoal. The preparation is then thoroughly dried with a continuously running oil pump. Yield: 1.35 g (99%); $R_f$ (silica gel, acetone): 0.5.

EXAMPLE 48

2,3-O-isopropylidene-5-O-trityl-D-ribose

For the preparation of 2,3-O-isopropylidene-5-O-trityl-D-ribose the method described by BREDERECK et al.[10] for the preparation of 5-O-trityl-$\alpha$-D-ribofuranose is used.

To a solution of 3.0 g (15.8 mmoles) of isopropylidene-ribose in 50 ml of absolute pyridine 4.4 g (15.8 mmoles) of trityl chloride are added and the mixture is stirred in a closed flask for 3 days at room temperature. The yellow-brown solution produced is poured into approximately 1 l of ice water. The brown sirup which separates is decanted off and is thoroughly mixed several times with water. Following this this sirup is dissolved in 50 ml of CHCl$_3$ and washed twice with KHSO$_4$-solution and 3 times with water. After drying over sodium sulfate the solvent is abstracted. A light brown sirup containing crystals remains. By crystallisation from methanol it is possible to obtain 1 g of triphenylcarbinol.

The remaining sirup is placed on a 30 cm silica gel column and first eluated with benzene; the non-polar by-products are separated. Following this 2,3-O-isopropylidene-5-O-trityl-D-ribose is eluated with benzene/acetone 50:50.

After removal of the solvent a light yellow foam is obtained. The product can then be caused to crystallise. Yield: 2.0 g (30%); $R_f$ (silica gel/benzene): 0.1.

EXAMPLE 49

1-hydrazino-2,3-isopropylidene-5-O-trityl-D-ribose

A solution of 1.7 g (4.0 mmoles) of 2,3-O-isopropylidene-5-O-trityl-D-ribose in 5 ml of absolute methanol is added dropwise while stirring and cooling in an ice bath slowly to a solution of 1.28 g (40 mmoles) of anhydrous hydrazine in 5 ml of absolute methanol. After a few minutes the ice bath is removed and the solution is stirred for 2.5 hours at room temperature. Following this the solvent is abstracted with superfluous hydrazine at room temperature and resulting yellow foam is freed of the last traces of hydrazine oil pump, under vacuum with a continuously operating oil pump.

EXAMPLE 50

3,5-dimethyl-1-(2.3-O-isopropylidene-5-O-trityl-$\beta$-D-ribofuranosyl)pyrazole 90/10).

To a solution of 1.5 g (3.36 mmoles) of 1-hydrazino-2,3-O-isopropylidene-5-O-trityl-D-ribose in 5 ml of absolute ethanol 336 mg (3.36 mmoles) of acetylacetone are added, also dissolved in 5 ml of absolute ethanol, and the mixture is stirred for 2 hours at room temperature. Then the solvent is abstracted. The remaining yellow sirup is subjected to chromatography (silica gel/methylene chloride). The first fraction obtained in this respect is again subjected to chromatography (silica gel/chloroform/acetone = 90/10). Yield: 450 mg (27%); $R_f$ (silica gel/CCl$_4$-acetone 90:10):0.6.

The second fraction obtained in the chromatography (silica gel/methylene chloride) is eluated with acetic acid. The substance mixture so obtained is again subjected to chromatography with cyclohexane/ether = 40/60 over a 60 cm silica gel column. Yield: 400 mg (24%); $R_f$ (silica gel/cyclohexane-ether = 40:60): 0.4.

EXAMPLE 51

1-(β-D-ribofuranosyl)pyrazolo [3,4-d]-pyrimidin-4-one 308 mg (1 mmole) 1-(2,3-O-isopropylidene-β-D-ribofuranosyl)pyrazolo-[3,4-d]-pyrimidin-4-one are dissolved in 20 ml of a mixture of acetone/water (10v/10v). To the solution 1 g of AMBERLITE IR-120 (H+-form) is added. After stirring for 24 hours, the ion-exchanger is separated by filtration and washed thoroughly with acetone/water and finally with water. The solvents of the combined solutions are removed in a rotary evaporator. The product is filtered off with a small quantity of ether and recrystallized from acetone. Melting point: 204° C; yield: 215 mg (80%).

EXAMPLE 52

5-amino-4-carbamolyl-1-(β-D-ribofuranosyl)pyrazole 1.49 g (5 mmoles) 5-amino-4-carbamoyl-1-(2,3,-O-isopropylidene-δ-D-ribofuranosyl)pyrazole are stirred in a mixture of 25 ml of water and 5 ml acetone with 1.5 g of AMBERLITE IR-120 (H+-form) for 2 hours at 65° C. A thin layer chromatography (silica gel; eluating medium: chloroform/methanol 80v/20v) then shows that all starting material has reacted quantitatively to the expected product. The ion exchanger is removed by filtration. By partially evaporating the solution a fine, very hygroscopic colorless powder is obtained.

EXAMPLE 53

5-amino-4-(N-benzoylcarbamoyl)-1-(2,3-O-isopropylidene-β-D-ribofuranosyl)pyrazole 11.71 g (60 mmoles) of 1-hydrazino-2,3-O-isopropylidene-D-ribose are dissolved in 200 ml of chloroform and while stirring, a solution of 12.20 g (50 mmoles) 2-ethoxy-1-cyano-N-benzoylacrylamide in 200 ml of chloroform is added at room temperature. 20 hours later the reaction mixture is boiled for 40 hours under reflux. The volume of the resulting solution is reduced to about 150 ml. From this solution an analytically pure product precipitates. After cooling to 0° C, the yield was 9.2 g. By further reducing the volume of the mother liquor and keeping it in an ice bath another 1.7 g of pure product can be isolated. Total yield: 10.9 g (54% relative to the acrylamide derivative). Melting point: 158°-160° C.

Literature

1. R. Barker and H.G. Fletcher, Jr., J. Org. Chem. 26, 4605 (1961)
2. A. Hampton, J. Amer. Chem. Soc. 83, 3640 (1961)
3. Suzuki, Katsumi; Kumashiro, Izumi; C.A. 71, 81698 z (1970)
4. T.A. Krenitsky, G.B. Elion, R.A. Strelitz and G. H. Hitchings, J. Biol. Chem. 242, 2675 (1967)
5. B.G. Hildick and G. Shaw, J. Chem. Soc. 1971 (C), 1610
6. B. Helferich and W. Schafer, Org. Syn. Coll., vol. I, 364 (1948)
7. M.E. Tate and C.T. Bishop, Can. J. Chem. 41 (7), 1801 (1963)
8. C.P.J. Glaudemans and H.G. Fletcher, Jr., J. Org. Chem. 28, 3004 (1963)
9. M.F. Evans et al., Carbohyd. Res. 3 (4), 453 (1967)
10. H. Bredereck, M. Kothnig and E. Berger, Chem. Ber. 73 956 (1940)
11. H. Bredereck, E. Berger and J. Ehrenberg, Chem.Ber. 73, 272 (1940)
12. S. Tejina and H.G. Fletcher, Jr., J. Org. Chem. 28, 2999 (1963).

What is claimed:

1. A compound of the formula

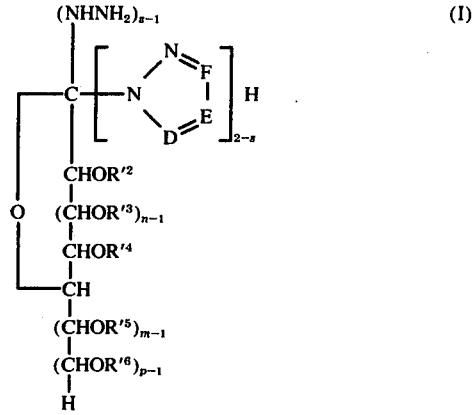

wherein
s is a positive whole number of at most 2;
D is =C(X)—, =C($NH_2$)- or =N-;
E is =C(Y)- or =N-;
F is =C(X)- or =N-; the residue

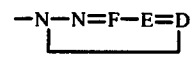

being aromatic;
W is -H, -OH or -$NH_2$;
X is -H, alkyl, phenyl or, together with Y, -N=CH-N=C(W)-;
Y is -H, carbethoxy, cyano, carbamoyl, formylcarbamoyl, benzoylcarbamoylor, together with one X, -C(W)=N-CH=N-;
each of
$n$, $m$ and $p$ is a positive whole number of at most 2, the sum of $n+m+p$ is at least 4, and at least one of f $n$, $m$ and $p$ is 1;
each of
$R'^2$, $R'^3$, $R'^4$, $R'^5$ and $R'^6$ is, independently, -H or a member selected from the group consisting of alkyl, ethylenically-unsaturated hydrocarbyl, aryl, aralkyl, and cycloalkyl having from 3 to 6 ring carbon atoms with the proviso that at least one of $R'^2$, $R'^3$, $R'^4$, $R'^5$ and $R'^6$, which is present in the compound, has a meaning other than -H or two respective radicals $R'^2$, $R'^3$, $R'^4$, $R'^5$ or $R'^6$ together denote alkylidene or benzylidene,
each alkyl, including the alkyl of each aralkyl, each ethylenically-unsaturated hydrocarbyl and each alkylidene having up to seven carbon atoms; each aryl and the aryl of each aralkyl being substituted or unsubstituted phenyl, substituted or unsubstituted α-naphthyl or substituted or unsubstituted β-naphthyl, any substituent of a substituted phenyl, a substituted α-naphthyl or a substituted β-naphthyl being a member selected from the group consisting of alkyl having up to seven carbon atoms, halo, nitro, trifluoromethyl, alkoxy having up to seven carbon atoms, hydroxy, sulfo, sulfino, alkylsulfone having up to seven carbon atoms, alkoxycarbonyl having up to seven carbon atoms, alkylamino having up to seven carbon atoms, dialkylamino having up to seven carbon atoms and carbamoyl; or,
when s denotes 2, an open-ring-form tautomer of such compound.

2. A member selected from the group consisting of a compound according to claim 1 and a counterpart thereof wherein two respective radicals $R'^2$, $R'^3$, $R'^4$, $R'^5$ or $R'^6$ together denote ring-substituted benzylidene, or ring substituent of which is a ring substituent selected from the group consisting of alkyl having up to 7 carbon atoms, halo, nitro, trifluoromethyl, alkoxy having up to 7 carbon atoms, hydroxy, sulfo, sulfino, alkylsulfone having up to 7 carbon atoms, alkoxycarbonyl having up to 7 carbon atoms, alkylamino having up to 7 carbon atoms, dialkylamino having up to 7 carbon atoms and carbamoyl.

3. A compound according to claim 2 of the formula:

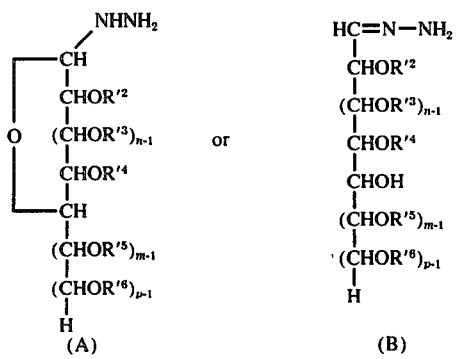

wherein each of
$n$, $m$ and $p$ is a positive whole number of at most 2, the sum of $n+m+p$ is at least 4, and at least one of $n$, $m$ and $p$ is 1;
each of $R'^2$, $R'^3$, $R'^4$, $R'^5$ and $R'^6$ is, independently, -H or a member selected from the group consisting of alkyl, ethylenically-unsaturated hydrocarbyl, aryl, aralkyl and cycloalkyl having from 3 to 6 ring carbon atoms, with the proviso 4. A compound according to claim 3 wherein each alkyl and each ethylenically-unsaturated hydrocarbyl has up to three carbon atoms, and each alkylidene is isopropylidene.

5. A hydrazino-aldopentose according to claim 3.

6. A hydrazino D-ribose according to claim 5 in open- or closed-ring form and wherein
$m$ is 2; each of $n$ and $p$ is 1;
$R'^2$ has one of the meanings of $R'^5$,
$R'^4$ has one of the meanings of $R'^5$,
$R'^5$ is -H or a member selected from the group consisting of alkyl, alkenyl, substituted or unsubstituted phenyl, substituted or unsubstituted naphthyl, ring-substituted or unsubstituted benzhydryl, ring-substituted or unsubstituted trityl, ring-substituted or unsubstituted benzyl, ring-substituted or unsubstituted α-naphthylmethyl and ring-substituted or unsubstituted β-naphthylmethyl;
any substituent being alkyl having up to seven carbon atoms, halo, nitro, trifluoromethyl, alkoxy having up to seven carbon atoms, hydroxy, sulfo, sulfino, alkylsulfone having up to seven carbon atoms, alkoxycarbonyl having up to seven carbon atoms, alkylamino having up to seven carbon atoms, dialkylamino having up to seven carbon atoms or carbamoyl, or, two respective radicals $R'^2$, $R'^4$ or $R'^5$ together denote alkylidene or ring-substituted or unsubstituted benzylidene.

7. The compound according to claim 6 which is 1-hydrazino-5-O-trityl-D-ribose.

8. The compound according to claim 6 which is 1-hydrazino-2,3-O-isopropylidene-5-trityl-D-ribose.

9. The compound according to claim 6 which is 1-hydrazino-2,3-O-isopropylidene-D-ribose.

10. The compound according to claim 6 which is 1-hydrazino-2,3,5-tri-O-benzyl-D-ribose.

11. A hydrazino D-arabinose according to claim 5 in open- or closed-ring form and wherein
$m$ is 2;
each of
$n$ and $p$ is 1;
$R'^2$ has one of the meanings of $R'^5$,
$R'^4$ has one of the meanings of $R'^5$, $R'^5$ is -H or a member selected from the group consisting of alkyl, alkenyl, substituted or unsubstituted phenyl, substituted or unsubstituted naphthyl, ring-substituted or unsubstituted benzhydryl, ring-substituted or unsubstituted trityl, ring-substituted or unsubstituted benzyl, ring-substituted or unsubstituted α-naphthylmethyl and ring-substituted or unsubstituted β-naphthylmethyl;
any substituent being alkyl having up to seven carbon atoms, halo, nitro, trifluoromethyl, alkoxy having up to seven carbon atoms, hydroxy, sulfo, sulfino, alkylsulfone having up to seven carbon atoms, alkoxycarbonyl having up to seven carbon atoms, alkylamino having up to seven carbon atoms, dialkylamino having up to seven carbon atoms or carbamoyl, or, two respective radicals $R'^2$, $R'^4$ or $R'^5$ together denote alkylidene or ring-substituted or unsubstituted benzylidene.

12. The compound according to claim 11 which is 1-hydrazino-2,3,5-tri-O-benzyl-D-arabinose.

13. A hydrazino-aldohexose according to claim 3.

14. A hydrazine-D-glucose according to claim 13 in open- or closed-ring form and wherein each of $m$ and $n$ is 2;
$p$ is 1;
$R'^2$ has one of the meanings of $R'^5$,
$R'^3$ has one of the meanings of $R'^5$,
$R'^4$ has one of the meanings of $R'^5$,
$R'^5$ is —H or a member selected from the group consisting of alkyl, alkenyl, substituted or unsubstituted phenyl, substituted or unsubstituted naphthyl, ring-substituted or unsubstituted benzhydryl, ring-substituted or unsubstituted trityl, ring-substituted or unsubstituted benzyl, ring-substituted or unsubstituted α-naphthylmethyl and ring-substituted or unsubstituted β-naphthylmethyl;
any substituent being alkyl having up to seven carbon atoms, halo, nitro, trifluoromethyl, alkoxy having up to seven carbon atoms, hydroxy, sulfo, sulfino, alkylsulfone having up to seven carbon atoms, alkoxycarbonyl having up to seven carbon atoms, alkylamino having up to seven carbon atoms, dialkylamino having up to seven carbon atoms or carbamoyl, or, two respective radicals $R'^2$, $R'^3$, $R'^4$ and $R'^5$ together denote alkylidene or ring-substituted or unsubstituted benzylidene.

15. The compound according to claim 14 which is 1-hydrazino-2,3,4,6-tetra-O-benzyl-D-glucose.

16. A compound according to claim 3 wherein the member is one which is readily split off, or two respective radicals $R'^2$, $R'^3$, $R'^4$, $R'^5$ or $R'^6$ together form a radical which is readily split off.

17. A compound according to claim 16 wherein said member is a ring-substituted or unsubstituted benzhydryl, trityl or benzyl group, or the alternative meaning, is benzylidene or isopropylidene.

18. A hydrazino-D-glucose according to claim 3 wherein at least one of $R'^2$ and $R'^5$ has a meaning other than -H.

19. A hydrazino-D-arabinose according to claim 3 wherein at least one of $R'^2$ and $R'^5$ has a meaning other than -H.

20. A hydrazino D-ribose according to claim 3 wherein at least one of $R'^2$ and $R'^5$ has a meaning other than —H; or $R'^2$ and $R'^4$, taken together, are isopropylidene.

21. A compound according to claim 2 wherein $s$ is 1.

22. A 5-amino-1-β-D-ribofuranosylpyrazole according to claim 21.

23. The compound according to claim 22 which is 5-amino-4-(N-formylcarbamoyl)-1-(2,3,5-tri-O-benzyl-β-D-ribofuranosyl)pyrazole.

24. The compound according to claim 22 which is 5-amino-4-(N-formylcarbamoyl)-1-(2,3-O-isopropylidene-β-D-ribofuranosyl)pyrazole.

25. The compound according to claim 22 which is 5-amino-4-carbamoyl-1-(2,3-O-isopropylidene-β-D-ribofuranosyl)pyrazole.

26. A compound according to claim 21 wherein X is H, alkyl or phenyl.

27. A compound according to claim 21 wherein one X, together with Y, is -N=CH-N=C(W)-.

28. A method for producing a compound according to claim 2, wherein $s$ is 1, or a counterpart thereof, wherein each R' is -H-, which comprises reacting a starting material, which is a compound according to claim 1, wherein $s$ is 2, with a compound which reacts, without cleavage, with the $H_2NNH$- of the starting material to yield a compound having an aromatic ring with 5 ring atoms, two adjacent ring atoms of which are the nitrogen atoms of said $H_2NNH$-, and, when the counterpart is desired, splitting off each member subsequently or during reaction.

29. A method according to claim 28 wherein the aromatic ring is of the formula

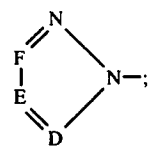

each of F and E is =C(H)—; D is =C(X)— or =N—; X is -H, alkyl or phenyl; and the method further comprises condensing an alicyclic hydrocarbon ring or a heterocyclic ring onto the 3,4-position of the aromatic ring.

30. A method according to claim 28 wherein the aromatic ring is of the formula

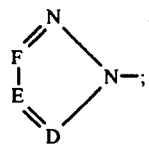

each of E and D is =C(H); F is =C(Z)- or =N-; Z is -H, alkyl or phenyl; and the method further comprises condensing an alicyclic hydrocarbon ring or a heterocyclic ring onto the 4,5-position of the aromatic ring.

31. A method according to claim 28 which comprises splitting off each member.

32. A method according to claim 28 in which the compound, wherein $s$ is 2, is a hydrazino-ribose, a hydrazinoarabinose or a hydrazino-glucose in which each member is readily split off, and the aromatic ring is a pyrazole ring.

33. A method according to claim 28 for the synthesis of β-anomers of pyrazole derivatives.

34. A method according to claim 28 for the synthesis of α-anomers of pyrazole derivatives.

35. A therapeutically-active and pharmacologically-acceptable compound according to claim 2, wherein $s$ is 1, or a physiologically-acceptable acid-addition salt thereof.

36. A pharmaceutical composition useful for treating gout which comprises a physiologically-acceptable carrier admixed with a sufficient concentration of a compound according to claim 35 to effect uric-acid level reduction in blood of a warm-blooded animal to which the composition is administered.

37. A method of reducing uric acid level in blood of a mammal which comprises administering to the mammal a non-toxic, but uric-acid-level reducing, amount of a composition according to claim 36.

38. A compound according to claim 21 wherein said residue comprises a 5-membered ring with 2 or 3 ring nitrogen atoms.

39. A compound according to claim 38 wherein E is =N-.

* * * * *

UNITED STATES PATENT OFFICE
CERTIFICATE OF CORRECTION

Patent No. 4,021,542            Dated May 3, 1977

Inventor(s) Richard Schmidt et al.            Page 1 of 4

It is certified that error appears in the above-identified patent and that said Letters Patent are hereby corrected as shown below:

Column 1, line 51 (directly below formula I) should read --and, if s denotes 2, also their ring form IB--. Column 2, line 40, "is" should read --is,--; line 41, "a propyl" should read --propyl--. Column 3, line 12, "for example" should read --, for example,--; line 14, "the" should read --of the--; line 15, "as" should read --as,--; line 55, "of hydrazinohexases" should read --of--; line 56, "hydrazino-hexoses" should read --hydrazinohexoses--. Column 4, line 4, "of the" should read --of--; "produced" should read --produced,--; line 27, "hydrazino-hexoses" should read --hydrazinohexoses--; line 30, "example" should read --example,--. Column 5, line 28, "No.) 1,720,024," should read --)1,720,024--. Column 6, line 2, "agents" should read --agents,--; line 4, "such" should read --, such--; "of" should read --or of--; line 6, "are" should read --are,--; line 48, "benzoyl)acryloamide," should read --benzoyl)acrylamide,--; line 57, "α-" should read --β- --. Column 7, line 22, "iropropylidene" should read --isopropylidene--; line 30, "Offenlengungsschrift" should read --Offenlegungsschrift--; line 31, "of the" should read --of--; line 50, ") and" should read --), and--. Column 8, line 12, "filter" should read --filler--; line 60, "solvents" should read --solvents,--. Column 9, lines 5 and 49 (each occurrence), "I$a$" should read --I$a$--; line 15, "of the" should read --of--; lines 15 and 51 (each occurrence) "I$b$" should read --I$b$--; lines 25 and 53 (each occurrence) "I$c$" should read --I$c$--; line 35, "I$b$" should read --IB--. Column 10, line 24, "exchanger" should read --exchange--; lines 29 to 30, "suspension in oil" should read --(suspended in oil)--; line

UNITED STATES PATENT OFFICE
CERTIFICATE OF CORRECTION

Patent No. 4,021,542           Dated May 3, 1977

Inventor(s) Richard Schmidt et al.        Page 2 of 4

It is certified that error appears in the above-identified patent and that said Letters Patent are hereby corrected as shown below:

50, "moles" should read --mmoles--. Column 11, line 13, "mmoles)" should read --mmoles) of--; line 20, "0,58" should read --0.58--; line 31, "n HCl" should read --N HCl--; line 49, "-anomer" should read --β-anomer--. Column 12, line 68, "pecipitate" should read --precipitate--. Column 13, line 18, "-trio" should read --tri--; line 43, "crystal" should read --crystals--; line 61, "oervaded" should read --pervaded--; line 62, "solutions" should read --solution--. Column 14, line 8, "anyhdrous" should read --anhydrous--; line 27, "55.5" should read --5.5--; line 30, "acetylacetone are added" should read --acetylacetone--; line 31, "THF)" should read --THF) are added; line 42, "-glucopyranoxyl" should read -- -glucopyranosyl--; line 44, "-glucopyrano-soyl)-" should read -- -glucopyranosyl)- --; line 45, "te" should read --the--; line 52, "glucopyranoxyl)" should read --glucopyranosyl)--;  line 60, "coloreless" should read --colorless--. Column 15, line 1, "$[\alpha]^{22}_{365}$" should read --$[\alpha]^{22}_{365}$--; line 5, "Oisopropylidene-" should read --O-isopropylidene- --; line 18, "assuems" should read --assumes--; line 25, "coloreless" should read --colorless--; line 44, "vary" should read --very--; line 47, "desire" should read --desired--. Column 16, line 5, "abosolute" should read --absolute--; line 22, "α" should read --β--;  line 30, "colum" should read --column--; line 34 (directly below line 33) should read --EXAMPLE 23--; line 46, "$OH^{116}$" should read --$OH^{\ominus}$--; line 55, "$578^{22}$" should read --$^{22}_{578}$--; line 58, "(2,30-" should read --(2,3-O- --; line 59, "ribofuranosyl)-pyrazole" should read --ribofuranosyl)pyrazole--. Column 17, line 14, "$H_gO$" should read --HgO--;

UNITED STATES PATENT OFFICE
CERTIFICATE OF CORRECTION

Patent No. 4,021,542      Dated May 3, 1977

Inventor(s) Richard Schmidt et al.      Page 3 of 4

It is certified that error appears in the above-identified patent and that said Letters Patent are hereby corrected as shown below:

Column 18, line 13, line 19, "and" second occurrence should read -- are --; line 44, "to" should read -- the --; "ribofuranoxyl" should read --ribofuranosyl--; line 20, "this" should read --this,--; line 27, "ribofuranoxyl)-pyrazole" should read --ribofuranosyl)pyrazole--; line 38, "OH⁻" should read --OH$^\ominus$--; line 67, "ribofuranosyl])-pyrazole" should read --ribofuranosyl)pyrazole--. Column 19, lines 48 and 49 should read --3,5-diethyl-1-(β-D-ribofuranosyl)pyrazole
   (a) 1.5 g (2.85 mmoles) of--; line 62, "10" should read --10 ml--. Column 20, line 12, "ribofuranosyl)-pyrazole" should read --ribofuranosyl)pyrazole--; line 34, "ribofuranosyl)-pyrazole" should read --ribofuranosyl)pyrazole--. Column 21, line 29, "rate it form" should read --rate it from formed--. Column 22, line 6, "one-four" should read --1/4--; line 15, "-[3,4-d-]" should read --[3,4-d]--; line 32, "White" should read --While--; line 38, "THF" should read --THF)--. Column 23, line 18, "b. 1.5 g..." should start a new paragraph; line 35, "produce" should read --product--; line 53, "this" should read --this,--. Column 24, line 3, "dimethyl]-1" should read --dimethyl-1- --. Column 25, line 11, "β" should read --α--; line 12, "arabinofuranosyl)-pyrazole" should read --arabinofuranosyl)pyrazole--;

line 36, "OH⁻" should read --OH$^\ominus$--. Column 26, line 30, "hydrazine oil pump," should read --hydrazine,--; line 36, "(2.3-O-" should read --(2,3-O- --; line 38, "pyrazole 90/10)." should read --pyrazole--. Column 27, line 9, "H⁺" should read --H$^\oplus$--; line 19, "-4-carbamolyl-1-" should read -- -4-carbamoyl-1- --; line 22, " -δ-" should read -- -β- --;

UNITED STATES PATENT OFFICE
CERTIFICATE OF CORRECTION

Patent No. 4,021,542      Dated May 3, 1977

Inventor(s) Richard Schmidt et al.      Page 4 of 4

It is certified that error appears in the above-identified patent and that said Letters Patent are hereby corrected as shown below:

line 24, "H$^+$" should read --H$^\oplus$--; line 39, "mmoles)" should read --mmoles) of--; line 46, "was" should read --is--. Column 28, line 40, "benzoylcarbamoylor," should read --benzoylcarbamoyl or,--; line 45, "$f\ n$" should read --$n$,--. Column 29, line 9, "or" should read --any--; line 43, "proviso." should read --proviso that at least one of R$'^2$, R$'^3$, R$'^4$, R$'^5$ and R$'^6$ which is present in the compound has a meaning other than -H, or two respective radicals R$'^2$, R$'^3$, R$'^4$, R$'^5$ or R$'^6$ together denote alkylidene or ring-substituted or unsubstituted benzylidene, each alkyl, each ethylenically-unsaturated hydrocarbyl and each alkylidene having up to seven carbon atoms.--. Column 31, line 47, "claim 1" should read --claim 2--.
Column 24, line 14, "hydrochlorie" should read --hydrochloride--.

Signed and Sealed this

Twenty-second Day of November 1977

[SEAL]

Attest:

RUTH C. MASON
Attesting Officer

LUTRELLE F. PARKER
Acting Commissioner of Patents and Trademark